US008933016B2

(12) United States Patent
Cowan et al.

(10) Patent No.: US 8,933,016 B2
(45) Date of Patent: Jan. 13, 2015

(54) METALLODRUGS HAVING IMPROVED PHARMACOLOGICAL PROPERTIES AND METHODS OF MANUFACTURE AND USE THEREOF

(71) Applicant: Metallopharm LLC, Delaware, OH (US)

(72) Inventors: James A. Cowan, Delaware, OH (US); Ada S. Cowan, Delaware, OH (US)

(73) Assignee: MetalloPharm, LLC, Delaware, OH (US)

(*) Notice: Subject to any disclaimer, the term of this patent is extended or adjusted under 35 U.S.C. 154(b) by 0 days.

(21) Appl. No.: 13/745,359

(22) Filed: Jan. 18, 2013

(65) Prior Publication Data

US 2013/0210705 A1   Aug. 15, 2013

Related U.S. Application Data

(60) Provisional application No. 61/588,077, filed on Jan. 18, 2012.

(51) Int. Cl.

| | | |
|---|---|---|
| *C07D 501/28* | (2006.01) | |
| *C07K 19/00* | (2006.01) | |
| *C07D 401/10* | (2006.01) | |
| *C07D 499/68* | (2006.01) | |
| *C07H 17/04* | (2006.01) | |
| *A61K 31/33* | (2006.01) | |
| *C07K 14/46* | (2006.01) | |
| *C07K 14/47* | (2006.01) | |
| *C07K 14/435* | (2006.01) | |

(52) U.S. Cl.
CPC .......... *C07D 501/28* (2013.01); *C07K 2319/20* (2013.01); *C07K 2319/00* (2013.01); *C07D 401/10* (2013.01); *A61K 31/33* (2013.01); *C07D 499/68* (2013.01); *C07H 17/04* (2013.01); *C07K 14/463* (2013.01); *C07K 19/00* (2013.01); *C07K 14/4723* (2013.01); *C07K 14/43563* (2013.01)
USPC .............. 514/2.3; 514/179; 514/209; 514/27; 514/253.08; 530/300; 540/333; 540/332; 540/230; 534/11; 534/15; 536/14; 544/363

(58) Field of Classification Search
CPC ... A01N 59/16; A01N 2300/00; A01N 25/10; C09D 175/08; C07K 16/44
See application file for complete search history.

(56) References Cited

U.S. PATENT DOCUMENTS

| | | | |
|---|---|---|---|
| 3,994,966 A | 11/1976 | Sundberg et al. | |
| 5,057,302 A | 10/1991 | Johnson et al. | |
| 5,326,856 A | 7/1994 | Coughlin et al. | |
| 5,480,970 A | 1/1996 | Pollak et al. | |
| 5,888,530 A | 3/1999 | Netti et al. | |
| 6,004,531 A | 12/1999 | Archer et al. | |
| 6,042,848 A | 3/2000 | Lawyer et al. | |
| 6,403,777 B1 | 6/2002 | Cowan | |
| 2004/0249122 A1 | 12/2004 | Blazyk | |
| 2008/0188422 A1 | 8/2008 | Cowan et al. | |
| 2009/0246150 A1 | 10/2009 | Reynolds et al. | |
| 2010/0316643 A1* | 12/2010 | Eckert et al. ............... | 424/134.1 |

FOREIGN PATENT DOCUMENTS

| | | | | |
|---|---|---|---|---|
| WO | WO 00/36136 | * | 6/2000 | ............... C12Q 1/00 |
| WO | 2005117997 A1 | | 12/2005 | |

OTHER PUBLICATIONS

Melino et al. Metal-Binding and Nuclease Activity of an Antimicrobial Peptide Analogue of the Salivary Histatin 5. Biochemistry 2006, 45, 15373-15383.*
Helmerhorst et al. Characterization of Histatin 5 with Respect to Amphipathicity, Hydrophobicity, and Effects on Cell and Mitochondrial Membrane Integrity Excludes a Candidacidal Mechanism of Pore Formation. J. Biol. Chem. Feb. 23, 2001;276(8):5643-9.*
Wang et al. Tobramycin-EDTA conjugate: a noninnocent affinity-cleaving reagent. Bioorg Med Chem Lett. Dec. 15, 1998;8(24):3665-70.*
Gusman et al. Is salivary histatin 5 a metallopeptide? Biochim Biophys Acta 2000. 1545:86-95.*
James A. Cowan. Catalytic metallodrugs. Pure Appl. Chem. 2008. vol. 80, No. 8, pp. 1799-1810.*
Alison Butler. Acquisition and Utilization of Transition Metal Ions by Marine Organisms. Science. Jul. 10, 1998;281(5374):207-10.*
Jenssen et al. Peptide Antimicrobial Agents. Clin Microbiol Rev. Jul. 2006;19(3):491-511.*
Li-Jun. Ming, Structure and Function of "Metalloantibiotics". Med Res Rev, 2003. 23, No. 6, 697-762.*
Zhang et al. Modification of Antimicrobial Peptide with Low Molar Mass Poly(ethylene glycol). J. Biochem. 2008;144(6)781-788.*
Vallee et al. Zinc: Biological Functions and Coordination Motifs. Acc. Chem. Res. 1993, 26, 543-551.*
Taber et al. Bacterial uptake of aminoglycoside antibiotics. Microbiol Rev. Dec. 1987;51(4):439-57.*
Ruissen et al., "Effects of histatin 5 and derived peptides on *Candida albicans*", Biochem. J., (2001) 356, 361-368.
International Search Report and Written Opinion issued in PCT/US2013/022198 dated May 15, 2013.
Gray et al., B/PI-derived synthetic peptides: synergistic effects in tethered bactericidal and endotoxin neutralizing peptides. Biochim Biophys Acta. May 11, 1995;1244(1):185-190.

(Continued)

*Primary Examiner* — Karlheinz R Skowronek
*Assistant Examiner* — Jia-Hai Lee
(74) *Attorney, Agent, or Firm* — Michael A. Whittaker; Yimei C. Hammond; Kremblas & Foster

(57) ABSTRACT

It is an object of the present invention to provide antimicrobial metallodrugs comprising an antimicrobial peptide ("AMP") and/or an antibiotic covalently bound to a metal binding moiety. These metallodrugs combine a metal binding domain which typically catalyzes oxido-reductase chemistry or acts as a Lewis-Acid catalyst, with a member of a diverse class of antimicrobial agents currently validated in preclinical and clinical settings for the treatment of a broad spectrum of pathogenic organisms.

22 Claims, 7 Drawing Sheets

(56) References Cited

OTHER PUBLICATIONS

Hocharoen and Cowan, Metallotherapeutics: Novel Strategies in Drug Design. Chemistry. Sep. 7, 2009;15 (35):8670-8676.

Mayo et al., Structure-function relationships in novel peptide dodecamers with broad-spectrum bactericidal and endotoxin-neutralizing activities. Biochem J. Aug. 1, 2000;349 Pt 3:717-728.

Melino et al., Metal-Binding and Nuclease Activity of an Antimicrobial Peptide Analogue of the Salivary Histatin 5. Biochemistry. Dec. 26, 2006;45(51):15373-15383.

Rozek et al., Structure of the Bovine Antimicrobial Peptide Indolicidin Bound to Dodecylphosphocholine and Sodium Dodecyl Sulfate Micelles. Biochemistry. Dec. 26, 2000;39(51):15765-15774.

Altman, et al., Bifunctional Chelating .Agents. Part 2. Synthesis of 1-(2-Carboxyethyl)ethylenediaminetetra-acetic Acid by Ring Cleavage of a Substituted Imidazole. J Chem Soc Perkin Trans I., 1984:59-62.

Altman, et al., Bifunctional Chelating Agents. Part 1. 1-(p-Aminophenethyl)-ethylenediaminetetra-acetic Acid. J Chem Soc Perkin Trans. I., 1983:365-368.

Andrews, Determination of minimum inhibitory concentrations. J Antimicrob Chemother. Jul. 2001;48 Suppl 1:5-16.

Brechbiel, et al., Synthesis of 1-(p-Isothiocyanatobenzyl) Derivatives of DTPA and EDTA. Antibody Labeling and Tumor-Imaging Studies. Inorg. Chem., 1986;25(16):2772-2781.

Conlon et al., Strategies for transformation of naturally-occurring amphibian antimicrobial peptides into therapeutically valuable anti-infective agents. Methods. Aug. 2007;42(4):349-357.

Findlay et al., Cationic Amphiphiles, a New Generation of Antimicrobials Inspired by the Natural Antimicrobial Peptide Scaffold. Antimicrob Agents Chemother Oct. 2010;54(10):4049-4058.

Gottler and Ramamoorthy, Structure, membrane orientation, mechanism, and function of pexiganan—A highly potent antimicrobial peptide design from magainin. Biochim Biophys Acta. Aug. 2009;1788(8):1680-1686.

Green, et al., Evaluation of PLED as a Chelating Ligand for the Preparation of Gallium and Indium Radiopharmaceuticals. Int J Nucl Med Biol. 1985;12(5):381-386.

Hohsaka and Sisido, Incorporation of non-natural amino acids into proteins. Curr Opin Chem Biol. Dec. 2002;6(6):809-815.

Koeth, Comparison of daptomycin MIC results by DIN, NCCLS, SFM, and SRGA methods for 297 Gram-positive organisms. Int J Antimicrob Agents. Jan. 2004;23(1):17-24.

Kroll, et al., Excretion of Yttrium and Lanthanum Chelates of Cyclohexane 1, 2-Trans Diamine Tetraacetic Acid and Diethylenetriamine Pentaacetic Acid in Man. Nature. Nov. 2, 1957;180(4592):919-920.

Long, Ni(II)•Xaa-Xaa-His Metallopeptide—DNA/RNA Interactions. Acc Chem Res 1999;32(10):827-836.

Meares and Goodwin, Linking Radiometals to Proteins with Bifunctional Chelating Agents. J Protein Chem., Apr. 1984;3(2):215-228.

Michael et al., Metal binding and folding properties of a minimalist Cys2His2 zinc finger peptide. Proc Natl Acad Sci U S A. Jun. 1, 1992;89(11):4796-4800.

Moi, et al., Copper Chelates as Probes of Biological Systems: Stable Copper Complexes With a Macrocyclic Bifunctional Chelating Agent. Anal Biochem. Jul. 1985;148(1):249-253.

Nelson and Griswold, A computer program for calculating antibody affinity constants. Comput Methods Programs Biomed. Jul.-Aug. 1988;27(1):65-68.

Polyakov et al., Novel Tat-Peptide Chelates for Direct Transduction of Technetium-99m and Rhenium into Human Cells for Imaging and Radiotherapy. Bioconjug Chem. Nov.-Dec. 2000;11(6):762-771.

Sundberg, et al., Selective Binding of Metal Ions to Macromolecules Using Bifunctional Analogs of EDTA. J Med Chem. Dec. 1974;17(12):1304-1307.

Taliaferro, et al., New Multidentate Ligands. 22. N ,N'-Dipyridoxylethylenediamine-N ,N'-diacetic Acid: A New Chelating Ligand for Trivalent Metal Ions. Inorg Chem. 1984;23(9):1188-1192.

van Erp et al., Application of a Sol Particle Immunoassay to the Determination of Affinity Constants of Monoclonal Antibodies. J Immunoassay. 1991;12(3):425-443.

Wang and Wang, APD: the Antimicrobial Peptide Database. Nucleic Acids Res. Jan. 1, 2004;32(Database issue): D590-592.

Wiegand et al., Agar and broth dilution methods to determine the minimal inhibitory concentration (MIC) of antimicrobial substances. Nat Protoc. 2008;3(2):163-175.

Wiradharma et al., Synthetic cationic amphiphilic α-helical peptides as antimicrobial agents. Biomaterials. Mar. 2011;32(8):2204-2212.

* cited by examiner

Fig. 1

| Strain | Metallodrug | MIC (µg/mL) for copper-bound drug [a] | MIC (µg/mL) for copper-free drug [a] | % reduction of glutathione for copper-bound versus copper-free drug [b] |
|---|---|---|---|---|
| E. coli ATCC 25922 | Cu-DOTAMP [c] | 32 | > 64 | 12 % |
|  |  |  |  |  |
| MRSA ATCC 43300 | Cu-PEP [d] | 2 | 2 | 19 % |
| E. coli ATCC 25922 | Cu-PEP | 2 | 2 | 7 % |
| P. aeruginosa ATCC 27583 | Cu-PEP | 2 | 4 | 8 % |

[a] While the MIC of the metal-bound DOTAMP and PEP complexes are similar to the metal free compounds, it is critical to have a new mode of action to prevent potential drug resistance.

[b] Assayed by use of Anaspec *Glutathione Cellular Assay Kit* Catalog # 72158, using drug concentration below the MIC

[c] Copper derivative of DOTA conjugate with ampicillin

[d] Copper derivative of an antimicrobial peptide. Cu-PEP is Cu-GGHGIRRIIRKIIHIIKK-amide.

FIG. 2B
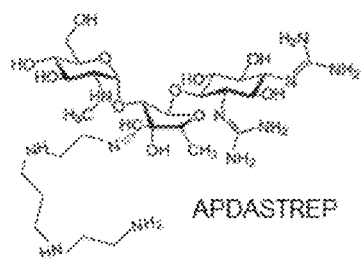
APDA-streptomycin
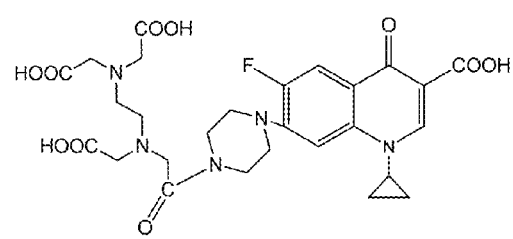
EDTA-CIPRO
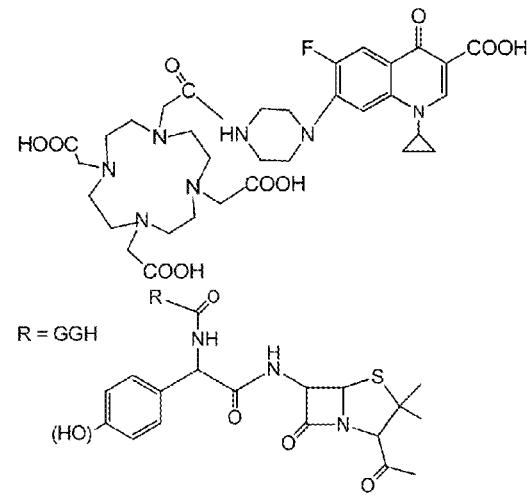
DOTA-CIPRO
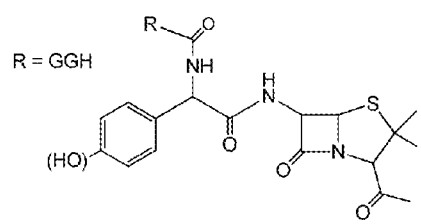
GGH-ampicillin (or amoxicillin)

US 8,933,016 B2

METALLODRUGS HAVING IMPROVED PHARMACOLOGICAL PROPERTIES AND METHODS OF MANUFACTURE AND USE THEREOF

The present application claims priority to U.S. Provisional Patent Application 61/588,077, filed Jan. 18, 2012, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Apr. 25, 2013, is named MET0002UT_SL.txt and is 23,527 bytes in size.

BACKGROUND OF THE INVENTION

The following discussion of the background of the invention is merely provided to aid the reader in understanding the invention and is not admitted to describe or constitute prior art to the present invention.

A search for alternatives to traditional antibiotics has led to the exploitation of reactive oxygen species for purposes of antimicrobial therapies. For example, photodynamic therapy, in which a photosensitizer such as methylene blue is targeted to a microorganism, followed by illumination with light to generate reactive oxygen species, has been shown to be effective against a broad spectrum of pathogens. Additionally, metals such as iron, copper, chromium, vanadium and cobalt are capable of redox cycling in which a single electron may be accepted or donated by the metal. This action catalyzes reactions that produce reactive radicals and can produce reactive oxygen species. For example, hydroxyl radical production by catalytic metal complexes can lead to modifications of amino acids (e.g. meta-tyrosine and ortho-tyrosine formation from phenylalanine), carbohydrates, initiate lipid peroxidation, and oxidize nucleobases. Metallodrugs, which typically comprise a metal binding moiety in a complex with a targeting moiety, take advantage of this redox cycling to generate reactive oxygen species. Not surprisingly, such metallodrugs have also been investigated for their antimicrobial capabilities. The development of such metallodrugs as therapeutic agents, however, has typically focused on the use of the targeting moiety to position the catalytic metal into close proximity with a target nucleic acid or protein, so as to take advantage of cleavage or modification of a specific target molecule.

"Oxidative stress" refers to toxic effects mediated by the production of peroxides and free radicals, causing non-specific damage to various components of the cell, including proteins, lipids, and DNA. Moreover, because reactive oxidative species can act as cellular messengers through a phenomenon called redox signaling, disturbances in the normal redox state of tissues can cause alterations both in conformation and activity of a number of enzymes. Phosphotyrosine phosphatases (PTPs) serve as important regulators of cellular signal transduction pathways. PTPs are sensitive targets of oxidative stress and may be inhibited by treatments that induce intracellular oxidation. The effects of PTP inactivation under oxidizing conditions are amplified by the redox-linked activation of key protein tyrosine kinases (PTKs), thus leading to the initiation of phosphotyrosine-signaling cascades that are no longer under normal receptor control.

An imbalance between the production of reactive oxygen species and a biological system's ability to readily remove such species or to repair the resulting damage can cause cell death; even moderate oxidation can trigger apoptosis, while more intense stresses may cause necrosis. The mammalian immune system takes advantage the lethal effects of oxidants by making production of oxidizing species a central part of its mechanism of killing pathogens; with activated phagocytes producing both ROS and reactive nitrogen species. These include superoxide (.O2-), nitric oxide (.NO) and their particularly reactive product, peroxynitrite (ONOO—). While the non-specificity of oxidative stress can prevent a pathogen from becoming resistant through mutation of a single molecular target, non-specific use of these highly reactive compounds in response to pathogens results in significant damage to host tissues.

SUMMARY OF THE INVENTION

It is an object of the present invention to provide antimicrobial metallodrugs comprising an antimicrobial peptide ("AMP"), or peptide that binds to a pathogenic target, covalently bound to a metal binding moiety. These metallodrugs combine a metal binding domain which typically catalyzes oxido-reductase chemistry or acts as a Lewis-Acid catalyst, with a member of a diverse class of antimicrobial agents currently validated in preclinical and clinical settings for the treatment of a broad spectrum of pathogenic organisms. Various linear, cyclic, and diastereomeric AMPs target pathogens through their physicochemical properties, rather than any specific amino acid sequence. Specifically, it is generally believed that AMP's mediate antimicrobial activity through one of three mechanisms—the amphiphilic topology causes insertion into, and disruption of, the cytoplasmic membrane of pathogens and cells harboring such pathogens; or the AMP interacts with negatively charged molecules such as nucleic acids and lipopolysaccharide (LPS), disrupting their activity; or the AMP interacts with target molecules within the pathogen, such as a protein involved in DNA transcription or replication, translation, or respiratory pathways, for example, and disrupt their activity. By incorporating a metal binding moiety to such peptides, these AMPs can be rendered more potent as antimicrobials through the ability to generate reactive oxygen species and oxidative stress as part of a "dual warhead" approach to antimicrobial therapeutics.

It is another object of the present invention to provide antimicrobial metallodrugs comprising an antibiotic covalently bound to a metal binding moiety. These metallodrugs combine a metal binding domain which typically catalyzes oxido-reductase chemistry or acts as a Lewis-Acid catalyst, with a member of a diverse class of antimicrobial agents currently validated in preclinical and clinical settings for the treatment of a broad spectrum of pathogenic organisms. Various antibiotics target pathogens through selective binding to bioactive macromolecules within a bacterial cell, typically based on structural resemblance to natural binding partners, and blocking the activity of these macromolecules. By incorporating a metal binding moiety to such antimicrobial agents, these antibiotic derivatives can be rendered more potent as antimicrobials through the ability to generate reactive oxygen species and oxidative stress as part of a "dual warhead" approach to antimicrobial therapeutics.

In a first aspect, the present invention provides antimicrobial compositions, comprising:
a first moiety comprising a polypeptide sequence that adopts an amphipathic structure (e.g. an AMP); and a metal binding moiety. In these compositions, the first moiety and the metal binding moiety are covalently linked to form a complex, preferably resulting in uptake of the complex into a pathogenic microorganism or within a cell of the subject which contains a pathogenic microorganism, which uptake is promoted by the AMP moiety of the metallodrug. Upon uptake of the complex, the metal binding moiety can generate reactive oxygen species, creating oxidative stress within the microorganism and/or cell, or function as a Lewis acid and generates reactive hydrolytic species within a pathogenic microorganism, wherein the concentration of hydrolytic species generated creates subsequent chemical stress within the pathogenic microorganism or cell of the subject to antimicrobial effect.

In a related aspect, the present invention relates to antimicrobial composition, comprising:
a first moiety which is (i) an antimicrobial peptide ("AMP"), or peptide that binds to a pathogenic target, the sequence of which is between 6 and 100 amino acids, is net positively charged, and is amphipathic, (ii) an antibiotic, or (iii) a conjugate comprising an AMP and an antibiotic; and
a second moiety which is a metal binding moiety, wherein the first moiety and the second moiety are covalently linked to form a complex. Preferably the first moiety promotes uptake of the complex into a target cell or organelle.

In various embodiments, the AMP portion of the composition adopts an amphipathic α-helical structure, adopts a structure comprising antiparallel β-sheets, adopts an extended backbone structure and/or adopts a ring structure. By way of example, α-helical peptides include GLFDIIKKI-AESI (SEQ ID NO: 1), FLPLIGRVLSGIL (SEQ ID NO: 2), FVQWFSKFLGRIL (SEQ ID NO: 3), IRRIIRKIIHIIKK (SEQ ID NO: 4), ILAWKWAWWAWRR (SEQ ID NO: 5), GWRTLLKKAEVKTVGKLALKHYL (SEQ ID NO: 6), and KGRGKQGGKVRAKAKTRSS (SEQ ID NO: 7); β-sheet peptides include WNLLRQAQEKFGKDKSP (SEQ ID NO: 8), FKCRRWQWRMKKLGAPSITCVRRAF (SEQ ID NO: 9), and VDKGSYLPRPTPPRPIYNRN (SEQ ID NO: 10); extended backbone peptides include ILPWKWPWWP-WRR (SEQ ID NO: 11); and ring peptides include FKCR-RWQWRMKKLGAPSITCVRRAF (SEQ ID NO: 12). This list is not meant to be limiting.

In certain embodiments, the first moiety comprises a naturally occurring polypeptide sequence which exhibits antimicrobial activity against an organism selected from the group consisting of a bacterium, a virus, a fungus, and a protozoan.

Examples of AMPs finding use in the present invention include Buforin, Pyrrhocoricin, ovispirin peptide OV-3, SMAP29, Histatin-5, Histatin-8, Histatin-2, CP10A, Bac2A, TriTrp1, Aurein 1.1, Magainin 1, Magainin 2, Indolicidin, and Bactenecin, and muteins thereof. This list is not meant to be limiting.

As noted above, it is an amphiphilic topology, and not a particular sequence, which is the feature of such AMPs. Folding into a stable α-helix separates the positive and hydrophobic amino acids in the sequence, resulting in an overall amphiphilic structure. Association with negatively charged phospholipids, or other pathogen target molecules, may induce this folding, and studies using circular dichroism (CD) have demonstrated that many AMPs are structured in their target membranes but may be disordered in simple buffered solutions. Various modifications to naturally occurring AMP sequences, such as amino acid modifications, the addition of lipid moieties, and generation of synthetic AMPs are well known in the art. See, e.g., Findlay et al., Antimicrob. Agents Chemother. 54: 4049-58, 2010; Wiradharma et al., Biomaterials 32: 2204-12, 2011; Gottler and Ramamoorthy, Biochim. Biophys. Acta 1788: 1680-6, 2009; Conlon et al., Methods 42: 349-57, 2007; each of which is hereby incorporated by reference in its entirety.

In various exemplary embodiments, the composition of the present invention is selected from the group consisting of

SEQ ID NO: 13:
GGHTRQARRNRRRRWRERQR

SEQ ID NO: 14:
KGHKTRQARRNRRRRWRERQR

SEQ ID NO: 15:
GGHTRSSRAGLQFPVGRVHRLLRK

SEQ ID NO: 16:
GGHGIRRIIRKIIHIIKK

SEQ ID NO: 17:
GGHGVRRFPWWWPFLRR

SEQ ID NO: 18:
GGHGILAWKWAWWAWRR

SEQ ID NO: 19:
GGHGRLARIVVIRVAR

SEQ ID NO: 20:
GGHGQRKLFFNLRKTKQRLGWFNQC

SEQ ID NO: 21:
GGHGEYVLRNWRIVKVATTKAC

SEQ ID NO: 22:
GGHGHPVHHYQ

SEQ ID NO: 23:
GGHGGHPVHHYQ

SEQ ID NO: 24:
GGHGLPLTPLP

SEQ ID NO: 25:
GGHGWRWYCR

SEQ ID NO: 26:
GGHTRQARRNRR

SEQ ID NO: 27:
GGHGLFDIIKKIAESI

SEQ ID NO: 28:
GGHFLPLIGRVLSGIL

SEQ ID NO: 29:
GGHFVQWFSKFLGRIL

SEQ ID NO: 30:
GGHGWRTLLKKAEVKTVGKLALKHYL

SEQ ID NO: 31:
GGHKGRGKQGGKVRAKAKTRSS

SEQ ID NO: 32:
GGHILPWKWPWWPWRR

SEQ ID NO: 33:
GGHVRRFPWWWPFLRR

SEQ ID NO: 34:
GGHFKCRRWQWRMKKLGAPSITCVRRAF

SEQ ID NO: 35:
GGHGIGKFLHSAGKFGKAFVGEIMKS

SEQ ID NO: 36:
GGHVDKGSYLPRPTPPRPIYNRN

SEQ ID NO: 37:
GGHGIRRIIRKIIHIIKKGGC

SEQ ID NO: 38:
GGHGVRRFPWWWPFLRRGGC

SEQ ID NO: 39:
GGHGILAWKWAWWAWRRGGC

```
SEQ ID NO: 40:
GGHRRWKIVVIRWRRGGC

SEQ ID NO: 41:
GGHFVQWFSKFLGRILGGC

SEQ ID NO: 42:
GGHILPWKWPWWPWRRGGC

SEQ ID NO: 43:
GGHIRRIIRKIIHIIKKGGC

SEQ ID NO: 44:
GGHVRRFPWWWPFLRRGGC

SEQ ID NO: 45:
GGHGRRWKIVVIRWRRGGC

SEQ ID NO: 46:
GGHWRWYCRGGK

SEQ ID NO: 47:
GGHGWRWYCRGGK

SEQ ID NO: 48:
NTATRQARRNRRRRWRERQR

SEQ ID NO: 49:
EDTATRQARRNRRRRWRERQR

SEQ ID NO: 50:
DOTATRQARRNRRRRWRERQR

SEQ ID NO: 51:
DTPATRQARRNRRRRWRERQR
```

The metal binding moiety in these sequences is at the N-terminus, bold and underlined (e.g., GGH and KGHK (SEQ ID NO: 68) peptide sequences), or italicized (representing NTA, EDTA, DOTA and DTPA as organic chelates). The C-terminus may be carboxylate, amide, or another derivative. In certain embodiments, the metal binding moiety in these sequences may be separated from the AMP sequence by a linkage chemistry, for example one or more bridging amino acids.

In a second aspect, the present invention provides antimicrobial compositions, comprising:
a first moiety comprising an antibiotic; and a metal binding moiety. In these compositions, the first moiety and the metal binding moiety are covalently linked to form a complex, preferably resulting in uptake of the complex into a pathogenic microorganism or within a cell of the subject which contains a pathogenic microorganism, which uptake is promoted by the antibiotic moiety of the metallodrug. Upon uptake of the complex, the metal binding moiety can generate reactive oxygen species, creating oxidative stress within the microorganism and/or cell, or function as a Lewis acid and generates reactive hydrolytic species within a pathogenic microorganism, wherein the concentration of hydrolytic species generated creates subsequent chemical stress within the pathogenic microorganism or cell of the subject to antimicrobial effect.

Examples of antibiotics finding use in the present invention include aminoglycosides, penicillins, cephalosporins, macrolides, sulfonamides, quinolones, tetracyclines and others. This list is not meant to be limiting. Various modifications to antibiotics are well known in the art and are hereby incorporated by reference in its entirety. Structures of exemplary antimicrobial compositions are presented in FIG. 2.

The metal binding moiety may be attached through standard crosslinking (e.g., EDC/NHS coupling) chemistry, or by imine formation and sodiumborohydride reduction in the case of APDA-streptomycin, or any standard conjugation methods. Examples of coupling chemistries are provided hereinafter. In certain embodiments, the metal binding moiety comprises a metal bound thereto, wherein said metal is redox-active in the bound state under oxidative conditions to generate one or more reactive oxygen species and/or the metal binding moiety has a metal bound thereto, wherein said metal is active as a Lewis acid catalyst in the bound state under hydrolytic conditions.

In various embodiments, the metal bound to the metal binding moiety is a cation of a metal selected from the group consisting of alkaline earth metals, metals which give rise to cations with an incomplete d sub-shell, lanthanide and actinide metals. In preferred embodiments, the transition metal is selected from the group consisting of Cu(II), Cu(III), Ni(II), Ni(III), Zn(II), Fe(II), Fe(III), Co(II), Co(III), Cr(II), and Cr(III).

The metal binding moieties of the present invention may be any chemistry which binds a metal in a catalytically active conformation. In certain embodiments, the metal binding moiety comprises an organic chelating ligand such as those known in the art using amine and carboxylate functionalities on the organic chelating ligand. By way of example, such an organic chelating ligand preferably coordinates a metal using the coordination chemistry of a compound selected from the group consisting of diethylenetriaminepentaacetic acid (DTPA), ethylenediamine tetraacetic acid (EDTA), N,N-bis(carboxymethyl)glycine (NTA), 1,4,7,10-tetraazacyclododecane-1,4,7,10-tetraacetic acid (DOTA), N,N'-Bis(2-aminoethyl)-1,3-propanediamine (APDA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC). This list is not meant to be limiting. Examples of metal chelate group structures are depicted in FIG. 3.

The compositions of the present invention are active against a variety of microbial targets selected from the group consisting of bacteria, funguses, protozoans, etc.

In other related aspects, the present invention provides methods for therapeutically inactivating a biochemical target, comprising:
administering to a subject in need thereof a composition according to the present invention under conditions wherein the composition generates reactive oxygen species within a pathogenic microorganism or within a cell of the subject which contains a pathogenic microorganism, wherein the concentration of reactive oxygen species generated creates oxidative stress within the pathogenic microorganism or cell of the subject to antimicrobial effect.

In other related aspects, the present invention provides methods for therapeutically inactivating a biochemical target, comprising:
administering to a subject in need thereof a composition according to the present invention under conditions wherein the composition generates reactive hydrolytic species within a pathogenic microorganism or within a cell of the subject which contains a pathogenic microorganism, wherein the concentration of hydrolytic species generated creates subsequent chemical stress within the pathogenic microorganism or cell of the subject to antimicrobial effect.

BRIEF DESCRIPTION OF THE FIGURES

FIG. 1 depicts the minimum inhibitory concentration (MIC) determined for exemplary compounds of the invention. FIG. 1 discloses "Cu-GGHGIRRIIRKIIHIIKK-amide" as SEQ ID NO: 80.

FIGS. 2A and 2B depict structures for exemplary compounds of the invention. FIG. 2A discloses "GGHCAMIK" and "GGHC-Amikacin" as SEQ ID NO: 79 and "GGHC" as SEQ ID NO: 76.

FIG. 3 discloses "KGHK" as SEQ ID NO: 68.

FIG. 4 discloses "Co-KGHK," "Ni-KGHK," and "Cu-KGHK" as SEQ ID NOS 81-83, respectively, in order of appearance.

FIG. 5 discloses "Co-KGHK," "Ni-KGHK," and "Cu-KGHK" as SEQ ID NOS 81-83, respectively, in order of appearance.

FIG. 6B discloses "Co-KGHK-Rev," "Ni-KGHK-Rev," and "Cu-KGHK-Rev" as SEQ ID NOS 81-83, respectively, in order of appearance.

Figure 2A:
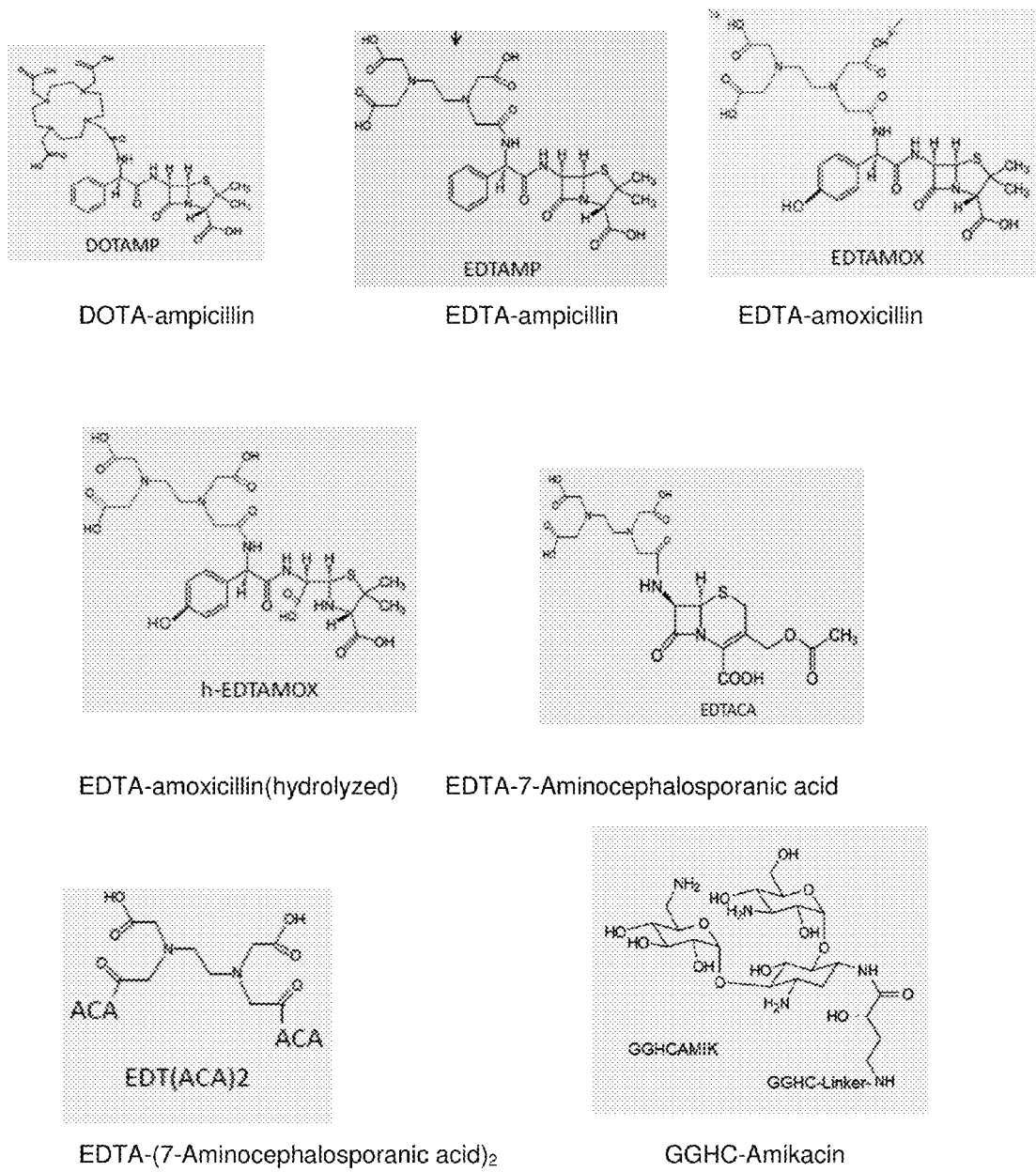

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The present invention relates to metallodrugs that combine a metal binding moiety and antimicrobial moiety. The antimicrobial moieties of the present compounds can provide antimicrobial activity through at least three distinct modes of action: some AMPs appear to act via enhanced permeability, disruption, or perforation of the membrane; while other AMPs do not appear to affect the membrane, but rather interact with unknown target(s), likely negatively charged molecules, such as nucleic acids and lipopolysaccharide (LPS); or interact with target molecules within the pathogen, such as a protein involved in DNA transcription or replication, translation, or respiratory pathways. Current antibiotics also function by interacting with proteins or nucleic acids of pathogens. By means of a metal species bound to such an antimicrobial moiety, the metallodrugs of the present invention can also exhibit antimicrobial effects through the oxidative stress due to generation of reactive oxygen species by a metal catalyst component, or function as a Lewis acid and generates reactive hydrolytic species within a pathogenic microorganism, wherein the concentration of hydrolytic species generated creates subsequent chemical stress within the pathogenic microorganism or cell of the subject to antimicrobial effect, thus providing a dual warhead approach to antimicrobial drugs.

DEFINITIONS

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

By "purified" and "isolated" is meant that a particular molecule or set of specified molecules accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of a composition. The weights of water, buffers, salts, detergents, reductants, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof, that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity."

Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immu-* noassay 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of an infection with a pathogenic organism.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.). "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. Depending on the context, "treatment" of a subject can imply that the subject is in need of treatment, e.g., in the situation where the subject comprises a disorder expected to be ameliorated by administration of a reagent.

Metal Binding Moieties

Suitable metal binding domains are described, for example, in U.S. Pat. Nos. 5,057,302; 5,326,856; 5,480,970; 6,004,531, 6,403,777; and in International Publication WO05/117997, each of which is hereby incorporated in its entirety, including all tables, figures and claims. Metallodrugs of the present invention may be formed by coupling of a first moiety to a metal binding domain through the use of bifunctional chelating agents. Such chelating agents comprising an array of metal-binding groups plus a moiety capable of covalent binding to a protein substrate are known art. Preferred are organic chelating groups which coordinate a metal using amine and carboxylate functionalities on the organic chelating group. Examples include compounds such as diethylenetriaminepentaacetic acid (DTPA), ethylenediamine tetraacetic acid (EDTA), N,N-bis(carboxymethyl)glycine (NTA), diethylenetriaminepentaacetate (DTPA), 1,4,7,10-tetraazacyclododecane-1,4,7,10-tetraacetic acid (DOTA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC), and derivatives thereof.

Diethylenetriaminepentaacetic acid (DTPA) and its derivatives comprise a backbone of three nitrogen atoms linked by two ethylene chains. Extending from the nitrogen atoms on the backbone are five carboxymethyl moieties. Methods have been described whereby one of the carboxymethyl groups may be reacted to form an amide bond with an amino acid residue present on an antibody or other protein molecule. The other four carboxymethyl moieties, together with the three nitrogen atoms, then remain available for metal binding.

In order to avoid the potential for such undesired cross-linking, bifunctional chelating agents incorporating a unique substrate reactive site have been developed. Ethylenediaminetetraacetic acid (EDTA) and its derivatives comprise a backbone of two nitrogen atoms linked by an ethylene chain. Extending from the nitrogen atoms on the backbone are four carboxymethyl moieties which with the nitrogen atoms are suitable for metal. Bifunctional chelating derivatives of EDTA are characterized by the attachment of a unique reactive function at a methylene carbon of the polyamine backbone. Sundberg, et al., J. Med. Chem. 17, 1304 (1974) discloses the synthesis of an EDTA derivative bearing a para-aminophenyl protein reactive substituent. This derivative may in turn be converted to bifunctional chelating agents capable of being coupled to protein substrates under mild conditions either by reaction of the amine with a portion of a chemically modified protein or by treatment of the primary amine to form other substituents capable of binding to protein substrates under mild conditions.

Meares, et al., J. Protein Chem., 3, 215-228 (1984) discloses methods whereby the para-aminophenyl derivative is converted to a diazonium derivative through nitrous acid treatment, to an isothiocyanate derivative by treatment with thiophosgene, to a bromoacetamide derivative by treatment with bromoacetylbromide and to a palmitaamidobenzyl derivative by treatment with palmitoyl chloride. Altman, et al., J. Chem. Soc. Perkin Trans. I., 365, 59-62 (1983) discloses a number of phenethyl analogues of the above EDTA compounds. See also, Sundberg, et al., U.S. Pat. No. 3,994, 966.

Cyclic chelating agents are known in the art. Kroll, et al., Nature, 180 919-20 (1957) discloses the use of cyclohexane-1,2-trans-diaminetetraacetic acid for the removal of heavy metal ions from the human body. Moi, et al., Anal. Biochem., 148, 249-253 (1985) discloses a macrocyclic bifunctional chelating agent precursor named 6-(p-nitrobenzyl)-1,4,8,11- tetra-azacyclotetradecane N,N',N'',N'''-tetraacetic acid (p-nitrobenzyl-TETA) which forms a copper chelate which is extremely stable in human serum under physiological conditions. In addition, the p-bromoacetamidobenzyl derivative of TETA shows high stability after conjugation to a monoclonal antibody. The Moi, et al. reference also discloses that improved metal binding yields may be obtained in some cases where the conjugate contains a spacer group between the protein and TETA.

Also of use in the present invention are the disclosures of Green, et al., Int. J. Nucl. Med. Biol., 12, 381-85 (1985) and Taliaferro, et al., Inorg. Chem. 23 1188-92 (1984) disclosing chelating agents. Green, et al. discloses a sexadentate ligand N,N'-dipyridoxylethylenediamine-N,N'-diacetic acid (PLED) complexed with gallium68 and indium111. Taliaferro, et al., discloses PLED chelates as well as those of N,N'-ethylene-bis[2-(o-hydroxy phenyl)glycine] (EHPG) and N,N'-bis(2-hydroxybenzyl)ethylenediamine-,N,N'-diacetic acid (HBED).

Other variations on known DTPA and EDTA derivatives include those of Brechbiel, et al., Inorg. Chem., 25, 2772-81 (1986) which discloses derivatives of DTPA wherein para-aminophenyl substituents are attached to the methylene carbons of the polyamine backbone. In addition, Altman, et al., J. Chem. Soc. Perkin Trans. I., 59 (1984) discloses a 2-carboxyethyl chelating derivative of EDTA.

In other examples, the metal binding domain may comprise an amino terminal Cu(II) and Ni(II) binding ("ATCUN") motif. The ATCUN motif comprises a peptide having (1) a free NH2-terminus, (2) two intervening peptide nitrogens, and (3) a histidine (H) residue at position 3. The ATCUN motif peptides are capable of binding metals such as Cu(II), Ni(II), Fe(III), Al(III), Co(II), and Co(III). Specific examples of ATCUN motifs include, but are not limited to, GGH, KGHK (SEQ ID NO: 68), VIHN (SEQ ID NO: 69), and YIHPF (SEQ ID NO: 70). FIG. 1 illustrates these specific ATCUN motifs with a metal M bound by the motif. In still another example—metal binding motif may lie internal to peptide sequence.

In still other examples, the metal binding domain may comprise the ATCUN motif having modifications with non-natural amino acids containing metal-binding groups. The modifications may be non-natural amino acids derived from modifications at the N- and C-termini of the ATCUN motif. For example cyclized lysines and pyridyl/pyrazolyl terminal secondary amino functionalities may be used.

Figure 3:
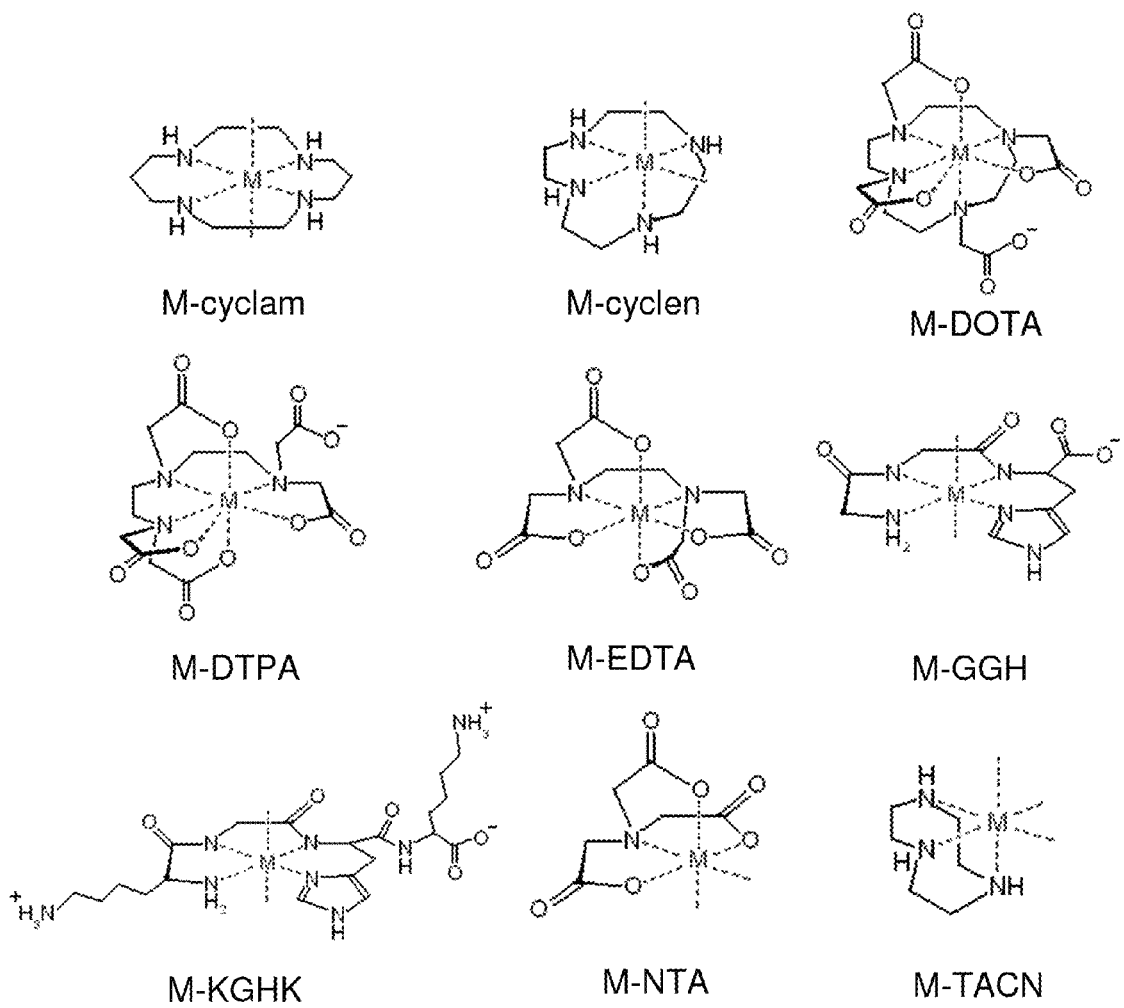
FIG. 3 depicts the structure of various metal binding moieties.

In yet another example, the N-terminus of a peptide may have an ATCUN motif thereon. A suitable N-terminus modification is described in Current Opinion in Chemical Biology 2002, 6, 809-815. The C-terminus of a peptide may have an ATCUN motif thereon. An example of a scheme for such a metal binding domain is illustrated in FIG. 2. This type of metal binding domain is discussed in Bioconjugate Chem. 2000, 11, 762-771. Another suitable metal binding domain is a peptide having an ATCUN motif on an internal portion of the peptide. A scheme for preparing one such domain is illustrated in FIG. 3 and discussed in Accounts of Chemical Research 1999, 32(10), 827. It will be understood that the peptide may be any suitable peptide of any suitable length. It will be further understood that the ATCUN motif may be any suitable motif.

In another example, metal binding domains having an ATCUN motif may be modified to enhance metal reactivity. The N-terminus of the ATCUN motif may be modified to replace primary amino functionality with secondary amino function. For example, a Schiff base may be utilized. In addition point variations of one or more of the amino acids in the ATCUN motif may be made (except the H is in the third position). For example, Xaa-G-H or G-Xaa-H may be used where Xaa represents any amino acid. In addition substitution of L-for D-configuration amino acids may be made for one or more of the amino acids in the ATCUN motif me. In both cases, such modifications may induce steric and electronic changes in the ATCUN motifs resulting in a modulation of metal reactivity.

In still other examples, the metal binding domain may comprise an octa-repeat motif from the prion protein having a sequence of PHGGGWGQ (SEQ ID NO: 71). In a further example, the metal binding domain may comprise a motif comprising histidine (H) as the first residue and glycine (G) as the third residue starting from the N-terminus of the motif. For example, the metal binding domain may comprise HGG, HGGG (SEQ ID NO: 72), HGGGG (SEQ ID NO: 73), HGGC (SEQ ID NO: 74), and the like. This domain may be repeated within a peptide sequence and cysteine (C) residues may be incorporated to increase metal binding affinity. It will be understood that the motif may comprise only a portion or portions of the metal binding domain. In another example, the metal binding domain may comprise a motif having histidine (H) as the third residue from the N-terminus. For example, the metal binding domain may comprise Xaa-Xaa-H with Xaa being any amino acid. The motif may be repeated in the metal binding domain, and the motif may comprise only a portion or portions of the metal binding domain. In one example, the metal binding domain may comprise a short peptide of less than about 30 amino acids containing a motif having H as the third residue and or a motif having H as the first residue and G as the third residue or having a motif of Xaa-H-Xaa-Gly-Xaa-anywhere within the sequence.

The metal binding domain may also comprise zinc finger peptides having a zinc binding unit comprising two cysteine (Cys) and two histidine (H is) residues. One such suitable zinc finger peptide is Lys-Tyr-Ala-Cys-Ala-Ala-Cys-Ala-Ala-Ala-Phe-Ala-Ala-Lys-Ala-Ala-Leu-Ala-Ala-His-Ala-Ala-Ala-His-Ala-Lys (SEQ ID NO: 75) which is reported in Proc Natl Acad Sci USA. 1992 Jun. 1; 89(11):4796-800. The metal binding domain may comprise short peptide conjugates with small molecular weight synthetic metal binding motifs. The small molecular weight synthetic metal binding motif may be selected to bind a desired metal. For example, the synthetic metal binding motif may comprise cyclam, bipyridyl, terpyridine, porphyrin, and TREN (tris(2-aminoethyl)amine). The metal binding domain may comprise Xaa-Xaa-cyclam/bipyridyl and the like. Additionally, the metal binding domain may comprise a peptide mimic with metal binding abilities.

In another example the metal binding domain may be a cyclam chelating motif.

The metal binding domain is preferably exposed to a desired metal so that the metal is bound to the metal binding domain and metal-ligand complexes may be formed. It will be understood that the metal binding domain may be exposed to the metal either before the formation of the ligand with the targeting domain or after the formation of the ligand. Any suitable metal may be used. Examples of suitable metals include transition metals such as Cu(II), Ni(II), Fe(III), Al(III), Co(II), Co(III), Zn (II), and other second and third row transition metal ions, and non-transition metals such as Al(III). The metal may be bound to the metal binding domain in any suitable manner. For example, a solution of 1 mM peptide in 10 mM Tris buffer (pH=7.4) may be mixed with 0.95 mM CuCl2 in 10 mM Tris buffer solution in a 1:1 ratio. It will be understood that any other suitable method may be used. Metal may also be recruited from intracellular or physiological environment.

Antimicrobial Moieties

Naturally occurring antimicrobial peptides (AMPs) and their mimics form a diverse class of antibacterial agents currently validated in preclinical and clinical settings for the treatment of infections caused by antimicrobial-resistant bacteria. Numerous studies with linear, cyclic, and diastereomeric AMPs have strongly supported the hypothesis that their physicochemical properties, rather than any specific amino acid sequence, are responsible for their microbiological activities. It is generally believed that the amphiphilic topology is essential for insertion into and disruption of the cytoplasmic membrane. In particular, the ability to rapidly kill bacteria and the relative difficulty with which bacteria develop resistance make AMPs and their mimics attractive targets for drug development. However, the therapeutic use of naturally occurring AMPs is hampered by the high manufacturing costs, poor pharmacokinetic properties, and low bacteriological efficacy in animal models.

Currently, the database of AMPs Wang and Wang, Nucl. Acids Red. 32: D590-D592, 2004) contains a listing of over 1,200 peptides. Those AMPs which adopt an amphiphilic α-helical structure in their target membrane are typically between 10 and 50 residues long and contain a mixture of both cationic and hydrophobic amino acids, distributed to distinct regions or faces of the α-helix. Positive charge drives association with negatively charged biological membranes via electrostatic interactions, and hydrophobic surfaces guide insertion into the membrane. Increasing hydrophobicity may increase antimicrobial activity, but is often accompanied by increased hemolytic activity.

Exemplary activity against organisms derived from data in the Antimicrobial Peptide Database for various AMPs are as follows:

```
                                                        (SEQ ID NO: 52)
TRSSRAGLQFPVGRVHRLLRK
active against Gram+ & Gram-, Fungi, Cancer cells (SEQ ID NO: 53)
GIRRIIRKIIHIIKK
active against Gram+ & Gram-, Fungi (SEQ ID NO: 54)
GVRRFPWWWPFLRR
active against Gram+ & Gram-, Fungi (SEQ ID NO: 55)
GILAWKWAWWAWRR
active against Gram+ & Gram-, Fungi, Virus, HIV (SEQ ID NO: 56)
GRLARIVVIRVAR
active against Gram+ & Gram- (SEQ ID NO: 57)
GIGKFLHSAGKFGKAFVGEIMKS
active against Gram+ & Gram-, Virus, Fungi, Parasites, Protozoan, HIV (SEQ ID NO: 58)
VDKGSYLPRPTPPRPIYNRN
active against Gram+ & Gram- (SEQ ID NO: 59)
GIRRIIRKIIHIIKKGGC
active against Gram+ & Gram-, Fungi GVR (SEQ ID NO: 60)
RFPWWWPFLRRGGC
active against Gram+ & Gram-, Fungi (SEQ ID NO: 61)
GILAWKWAWWAWRRGGC
active against Gram+ & Gram-, Fungi, Virus, HIV (SEQ ID NO: 62)
RRWKIVVIRWRRGGC
active against Gram+ & Gram- (SEQ ID NO: 63)
FVQWFSKFLGRILGGC
active against Gram+ & Gram-, Virus, Parasites, Protozoan (SEQ ID NO: 64)
ILPWKWPWWPWRRGGC
active against Gram+ & Gram-, Fungi, Virus, HIV (SEQ ID NO: 65)
IRRIIRKIIHIIKKGGC
active against Gram+ & Gram-, Fungi (SEQ ID NO: 66)
VRRFPWWWPFLRRGGC
active against Gram+ & Gram-, Fungi
```

GRRWKIVVIRWRRGGC (SEQ ID NO: 67)
active against Gram+ & Gram−

A significant drawback of AMPs is their protease susceptibility, which can result in decreased bioavailability. Incorporation of d-amino acids creates enantiomeric peptides which behave similarly to their l-amino acid counterparts which tend to be slightly less active against bacteria, though beneficial reductions in hemolytic activity have been observed. Any loss of in vitro activity appears to be balanced by reduced susceptibility to in vivo degradation.

In addition to the incorporation of metal-binding moieties into AMPs, additional functionalities may also be included. For example, aminoglycoside antibiotic-derived amphiphiles (AADAs) exhibit Gram-positive coccal activity against methicillin-resistant *Staphylococcus epidermidis* (MRSE) (MIC, 0.5 µg/ml) and methicillin-resistant *Staphylococcus aureus* (MRSA) (MIC, 1 µg/ml). The AADAs are believed to mimic the physicochemical and amphiphilic properties of AMPs by combining the cationic nature of aminoglycosides with hydrophobic side groups. The side groups are attached to auxiliary hydroxides via an amide bond or via carbamate or ether linkages. The AADAs may retain the RNA-binding properties of aminoglycoside antibiotics, resulting in a dual warhead function. The addition of a metal-binding domain can generate a "triple warhead" antibiotic.

Suitable antimicrobial moieties may also be selected from amongst the known classes of antibiotics. Antibiotics are commonly classified based on their mechanism of action, chemical structure, or spectrum of activity, and include, but are not limited to, aminoglycosides (e.g., gentamicin, kanamycin, kanamycin, paromomycin), ansamycins (e.g., geldanamycin), carbacephems (e.g., loracarbef), carbapenems (e.g., ertapenem, doripenem), cephalosporins (e.g., cefalexin, cefoxitin, cefixime, cefepime, ceftobiprole), peptidoglycan-inhibiting glycopeptides (e.g., vancomycin, telavancin), lincosamides (e.g., clindamycin), gram positive-directed lipopeptides (e.g., daptomycin), macrolides (e.g., erythromycin, azithromycin, telithromycin), monobactams (e.g., aztreonam), nitrofurans (e.g., furazolidone), penicillins (e.g., amoxicillin, carbenicillin, penicillin G), quinolones (e.g., ciprofloxacin, enoxacin), sulfonamides (e.g., trimethoprim, sulfamethoxazole), tetracyclines (e.g., tetracycline, minocycline, doxycycline), mycobacterial-inhibiting compounds (e.g., clofazimine, capreomycin, ethambutol, isoniazid, rifampicin, streptomycin), chloramphenicol, fosfomycin, metronidazole, and timidazole.

Chemical Coupling

The metal binding and ligand moieties of the present invention may be coupled using chemical linkages well known in the art. Chemical cross-linkers are discussed in numerous books and catalogues. See, e.g., Wong, *Chemistry of Protein Conjugation and Cross-linking*, CRC Press, Boca Raton, Fla., 1991. These reagents often employ functional groups that couple to amino acid side chains of peptides. Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety for inclusion in a sterol may be made empirically in order to best preserve a biological property of interest (e.g., binding affinity of an antibody, catalytic activity of an enzyme, etc.)

Coupling Through Amine Groups:

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

Coupling Through Sulfhydryl Groups:

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

Coupling Through Carboxyl Groups:

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

Nonselective Reactive Groups:

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

Coupling Through Arginines:

Glyoxals are useful compounds for targeting the guanidinyl portion of arginine residues. Glyoxals will target arginines at mildly alkaline pH. There is some cross-reactivity (the greatest at higher pH) with lysines.

Coupling Through Carbonyl Groups:

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones. For carbohydrates with reducing end(s), the carbonyl group(s) can be reactive towards a hydrazine moiety to form a hydrazone bond. S-HyNic is a heterobifunctional linker used to incorporate HyNic (6-hydrazinonicotinamide) moieties into molecules through a free amino group via an activated ester (i.e. NHS). The addition of a HyNic hydrazine linker permits formation of a conjugate in slightly acidic buffer (100 mM NaPO4, pH6). For carbohydrates without a reducing end, CDAP specific activation may be used. Under mild conditions (pH 9.5 for activation and pH 7 for conjugation), 1-cyano-4-dimethylaminopyridinium tetrafluoroborate ("CDAP") converts hydroxyl groups to cyanyl esters which will then form carbamates in the presence of amine groups.

Polymeric substances may be optionally included in the linkage chemistry and/or in one of the functional moieties being linked. In one example, such polymeric substances are preferably poly(alkylene oxides). As used herein, the term "alkylene oxide" refers to the structure, —X—O—, where X is an alkylene moiety covalently linked to oxygen 0; thus poly(alkylene oxide) refers to the structure —(X—O—)$_m$)—. It is preferred that the poly(alkylene oxide) polymer be a nonbranched homopolymer (i.e., a polymer of the structure —((CH$_2$)$_n$—O—)$_m$)— in which n does not vary) such as poly(ethylene oxide) derived from ethylene glycol. Alternative polymers such as other polyalkylene oxide homopolymers (e.g., methylene oxide, propylene oxide, isopropylene oxide, and butylene oxide polymers) and co-polymers or block co-polymers of poly(alkylene oxides) may also be used. In those aspects of the invention where PEG-based polymers are used (PEG=Poly(ethylene glycol)), it is preferred that they have average length n of between 4 and 1000 monomeric units. Molar equivalent amounts of the other alkylene oxides may be determined readily by those of ordinary skill in the art to arrive at preferred average molecular weights for other homopolymers and copolymers.

Average molecular weights of the present invention are measured using the "number-average" method. In a mixture of polymer molecules with different molecular weights in which the number of molecules having a particular molecular weight, $M_i$, is given by $N_i$, the "number-average" probability of a given mass being present is $$P_i = \frac{N_i}{\sum_{j=0}^{\infty} N_j}$$

and the number-average molecular weight is given by the formula $$\overline{M_n} = \sum_{i=0}^{\infty} \left( \frac{N_i}{\sum_{j=0}^{\infty} N_j} \right) M_i = \frac{\sum_{i=0}^{\infty} N_i M_i}{\sum_{j=0}^{\infty} N_j}$$

The number average is the simple arithmetic mean, representing the total weight of the molecules present divided by the total number of molecules. The number-average molecular weight of a polymer may be measured by vapor pressure osmometry using methods and apparatuses well known to those of skill in the art.

Alternative polymeric substances which may be used in place of poly(alkylene oxides) include materials such as dextran, polyvinyl pyrrolidones, polysaccharides, starches, polyvinyl alcohols, polyacryl amides or other similar polymers. Those of ordinary skill in the art will realize that the foregoing is merely illustrative and not intended to restrict the type of non-antigenic polymeric substances suitable for use herein.

Pathogenic Targets

As noted herein, in various embodiments, a metallodrug of the invention are suitable for use as antimicrobial therapeutics in a subject. In general, target microbes can be any pathogen including without any limitation bacteria, yeast, fungi, eukaryotic parasites, etc. In various embodiments, compounds of the invention are used to treat infection by pathogen/infectious agents which include, but are not limited to, *Mycobacterium* (*Mycobacterium tuberculosis*, *M. bovis*, *M. avium-intracellulare*, *M. leprae*), *Pneumococcus*, *Streptococcus*, *Staphylcococcus*, *Corynebacteria Listeria*, *Erysipelothrix*, *Bacillus* (e.g., *B. anthracis*), *Clostridium* (e.g., *C tetani*, *C. perfringens*), Mixed Anaerobes, *Neisseria*, *Salmonella*, *Shigella*, *Hemophilus*, *Burkholderi*, *Escherichia* (e.g., *E. coli*), *Klebsiella*, *Enterobacter*, *Serratia*, *Pseudomonas*, *Bordatella*, *Francisella* (e.g., *F. tularensis*), *Yersinia*, *Vibrio* (e.g., *V. cholerae*), *Bartonella*, *Legionella*, *Spirochaetes* (*Treponema*, *Leptospira*, *Borrelia*), Fungi, *Actinomyces*, *Rickettsia*, *Mycoplasma*, *Chlamydia*, Protozoa (including *Entamoeba*, *Plasmodium*, *Leishmania*, *Trypanosoma*, *Toxoplasma*, *Pneumocystis*, *Babasia*, *Giardia*, *Cryptosporidium*, *Trichomonas*), Helminths (*Trichinella*, *Wucheraria*, *Onchocerca*, *Schistosoma*, *Nematodes*, *Cestodes*, *Trematodes*).

Each of the foregoing and subsequent lists is illustrative, and is not intended to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide. slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA).

EXAMPLES

The following examples serve to illustrate the present invention. These examples are in no way intended to limit the scope of the invention.

Example 1

A conjugate of DOTA with ampicillin was formed by standard 1-Ethyl-3-[3-dimethylaminopropyl]carbodiimide hydrochloride (EDC) coupling methods and copper coordinated in solution by addition of aqueous copper ion following HPLC purification. Ampicillin sodium salt was from Fisher BioReagents (MW 371.4). DOTA-NHS-ester was from Macrocylic (DOTA-NHS-ester. HPF6.3CF3COOH, MW 990). All other reagents and solvents were of the highest available purity and used as purchased.

In an eppendorf tube, 8 mg of Ampicillin (Na salt, 0.022 mmole, 2× excess) was dissolved in 200 µL dry DMSO. The solution was added into a small glass crimp cap vial with rubber septum containing 8 mg DOTA-NHS-ester (0.011 mmole). The reaction mixture was purged with argon for 5 min, and it was mixed overnight at room temperature using a small stirring bar.

DOTA-Ampicillin was purified from the reaction mixture using two different chromatographic techniques. In the first step, anionic-HPLC purification was carried out on a Poly-WAX LP column (4.6×250 mm, from PolyLC Inc.). Before anionic-HPLC, 1 mL of 20 mM Tris buffer pH7.3 was added to the reaction mixture and pH was adjusted to ~7.3 by addition of 1M NaOH. The sample was applied to the anionic column, previously equilibrated with 20 mM Tris pH7.3. The column was washed with the equilibrium buffer (5 min, 0.7 mL/min), then by a linear gradient of NaCl using Tris 20 mM+1M NaCl pH7.3 (1% NaCl/min). All of the peaks from anionic-HPLC were collected and analyzed by ESI. The fractions containing product (33-40 min, DOTA-Ampicillin, 734.3, -mode) were pooled and applied to a reversed phase column (C18 Semi-prep, 10×250 mm, Vydac) without any TFA in the solvents (Water and acetonitrile). The fraction containing the product from RP column was concentrated in Speed-Vac to remove the acetonitrile. The concentration of DOTA-ampicillin in the final solution was determined using Ni titration method. The copper chelate of the product (Cu-DOTAMP) was made and used for further studies.

The influence of this compound on cellular oxidative stress was assayed by use of Anaspec Glutathione Cellular Assay Kit Catalog #72158, using drug concentration below the MIC. FIG. 1 shows the significant decrease in concentration of reduced cellular glutathione (~12%) following addition of Cu-DOTAMP to the medium, relative to the copper free compound. The MIC values for DOTAMP materials were also determined in several bacteria detailed in a later summary Table.

Example 2

Synthesis of EDTA-Amoxicillin (EDTAMOX)

Amoxicillin was obtained from MP Biomedicals (MW 365.4). EDTA (free acid) was from Aldrich (MW 292.24) and EDC from TCI America. All other reagents and solvents were of the highest available purity and used as purchased.

In a small glass crimp cap vial with rubber septum, 12 mg EDTA (0.041 mmole) was mixed with 300 µL dry DMSO. The mixture was heated on a hot-plate to complete dissolution of EDTA. After cooling down the solution to room temperature, 8 mg of EDC (0.042 mmole) was added and mixed at room temperature for 30 min. Then, 5 mg of NHS (0.043 mmole) was added to the mixture and mixed for another 30 min. 18.3 mg amoxicillin (0.05 mmole) was added to activated EDTA, and the reaction was mixed overnight at room temperature (pH 7-8).

EDTA-Amoxicillin was purified from the reaction mixture using two different chromatographic techniques. In the first step, anionic-HPLC purification was carried out on a Poly-WAX LP column (4.6×250 mm, from PolyLC Inc.). Before anionic-HPLC, 1 mL of 20 mM Tris buffer pH7.3 was added to the reaction mixture and pH was adjusted to ~7.3 by addition of 1M NaOH. The sample was applied to the anionic column (2 runs), previously equilibrated with 20 mM Tris pH7.3. The column was washed with the equilibrium buffer (10 min, 0.7 mL/min), then by a linear gradient (0 to 0.56 M NaCl in 80 min) using buffer Tris 20 mM+1M NaCl pH7.3. Fractions collected from anionic-HPLC were analyzed by ESI. The fractions containing product (43-52 min) were applied to a reversed phase column (C18 Semi-prep, 10×250 mm, Vydac) without any TFA in the solvents (Water and acetonitrile). The fraction containing the product from RP column was concentrated in Speed-Vac to remove the acetonitrile. EDTA-amoxicillin was quantitated in the final solution using Ni titration method. The copper chelate of the product (Cu-EDTAMOX) was prepared and used for further studies.

The last fraction of anionic-HPLC (55-60 min) showed the MW of 657.2 in ESI which could be the hydrolyzed-EDTA-amoxicillin (639.6+18). It was purified using RP-HPLC and the product hEDTAMOX was quantitated. The Cu-hEDTAMOX was prepared and used for further studies.

Example 3

Synthesis of EDTA-7-Aminocephalosporanic acid (EDTACA)

7-Aminocephalosporanic acid was obtained from Fisher BioReagents (MW 272.3). EDTA (free acid) was from Aldrich (MW 292.24) and EDC from TCI America. All other reagents and solvents were of the highest available purity and used as purchased.

In a small glass crimp cap vial with rubber septum, 12 mg EDTA (0.041 mmole) was mixed with 300 µL Dry DMSO. The mixture was heated on a hot-plate to complete dissolution of EDTA. After cooling down the solution to room temperature, 8 mg of EDC (0.042 mmole) was added and mixed at room temperature for 30 min. Then, 5 mg of NHS (0.043 mmole) was added to the mixture and mixed for another 30 min. 13.6 mg amoxicillin (0.05 mmole) was added to activated EDTA, and the reaction was mixed overnight at room temperature (pH 7-8).

EDTACA was purified from the reaction mixture using two different chromatographic techniques. In the first step, anionic-HPLC purification was carried out on a PolyWAX LP column (4.6×250 mm, from PolyLC Inc.). Before anionic-HPLC, 1 mL of 20 mM Tris buffer pH7.3 was added to the reaction mixture and pH was adjusted to ~7.3 by addition of 1M NaOH. The sample was applied to the anionic column (2 runs), previously equilibrated with 20 mM Tris pH7.3. The column was washed (0.7 mL/min) with a linear gradient (0 to 0.5 M NaCl in 60 min) using buffer Tris 20 mM+1M NaCl pH7.3. Fractions collected from anionic-HPLC were analyzed by ESI. The fractions containing product (20-26 min) were pooled and applied to a reversed phase column (C18 Semi-prep, 10×250 mm, Vydac) without any TFA in the solvents (Water and acetonitrile). The fraction containing the product from RP column was concentrated in Speed-Vac to remove the acetonitrile. EDTA-7-aminocephalosporanic acid (EDTACA) was quantitated in the final solution using Ni titration method. The copper chelate of the product (Cu-EDTAMP) was prepared and used for further studies.

The fraction at 33-37 min in anionic-HPLC showed the MW of 800 in ESI which is the EDTA coupled to two molecules of 7-aminocephalosporanic acid (EDT(ACA)2) (292+2(272)−2(18)=800). It was purified using RP-HPLC and the product EDT(ACA)2 was quantitated. The Cu-EDT(ACA)2 was prepared and used for further studies.

Example 4

Synthesis of EDTA-Ampicillin (EDTAMP)

Ampicillin sodium salt was from Fisher BioReagents (MW 371.4). EDTA (free acid) was from Aldrich (MW 292.24).

EDC was purchased from TCI America. All other reagents and solvents were of the highest available purity and used as purchased.

In a small glass crimp cap vial with rubber septum, 12 mg EDTA (0.041 mmole) was mixed with 300 μL dry DMSO. The mixture was heated on a hot-plate to complete dissolution of EDTA. After cooling down the solution to RT, 8 mg of EDC (0.042 mmole) was added and mixed at RT for 30 min. Then, 5 mg of NHS (0.043 mmole) was added to the mixture and mixed for another 30 min. 18.6 mg ampicillin-Na (0.05 mmole) was added to activated EDTA, and the reaction was mixed overnight at RT (pH 7-8).

EDTA-Ampicillin was purified from the reaction mixture using two different chromatographic techniques. In the first step, anionic-HPLC purification was carried out on a Poly-WAX LP column (4.6×250 mm, from PolyLC Inc.). Before anionic-HPLC, 1 mL of 20 mM Tris buffer pH7.3 was added to the reaction mixture and pH was adjusted to ~7.3 by addition of 1M NaOH. The sample was applied to the anionic column (2 runs), previously equilibrated with 20 mM Tris pH7.3. The column was washed with the equilibrium buffer (10 min, 0.7 mL/min), then by a 60 min linear gradient of NaCl using Tris 20 mM+1M NaCl pH7.3 (1% NaCl/min). All of the peaks from anionic-HPLC were collected and analyzed by ESI. The fractions containing product (35-45 min) were pooled and applied to a reversed phase column (C18 Semi-prep, 10×250 mm, Vydac) without any TFA in the solvents (Water and acetonitrile). The fraction containing the product from RP column was concentrated in Speed-Vac to remove the acetonitrile. EDTA-ampicillin was quantitated in the final solution using Ni titration method. The copper chelate of the product (Cu-EDTAMP) was prepared and used for further studies.

Example 5

Synthesis of APDA-Streptomycin (APDASTREP)

Streptomycin sulfate (MW 1457.4) and Sodium borohydride were from Sigma. N,N'-Bis(2-aminoethyl)-1,3-propanediamine (APDA) (MW 160.27) was from Kodak. All other reagents and solvents were of the highest available purity and used as purchased.

In a glass crimp cap vial with rubber septum, 500 μL of APDA (3 mmole) was dissolved in 3 mL of 100 mM carbonate buffer pH 8.65. 500 mg of Streptomycin sulfate (0.34 mmole) was added to APDA solution. pH of the mixture was ~10. The reaction was mixed at RT for 24 h under argon. ESI of the reaction mixture showed the presence of coupling product (MW=724) in the solution (m/z 724.5, 362.8). Sodium borohydride (300 mg) was added to the reaction and mixed at RT for 48 h. ESI of the reaction mixture after reduction with NaBH4 approved the addition of two hydrogen atoms to imine (C=N) bond (m/z 726.6, 363.8).

Purification of APDASTREP was carried out using cationic-HPLC on a PolyCAT A column (4.6×250 mm, from PolyLC Inc.). Acetonitrile (1 mL) was added to 500 uL of reaction mixture and vortexed. A biphasic mixture was formed. The upper phase (colorless) was discarded and the lower phase (yellow) containing the product was kept for HPLC. Before running the HPLC, 500 μL of equilibration buffer (sodium phosphate 10 mM pH5.4 containing 55% acetonitrile) was added to the sample and applied to the cationic column. The column was washed (0.7 mL/min) with a linear gradient (0 to 0.45 M NaCl in 30 min) using buffer Na-phosphate 10 mM pH5.4 containing 1M NaCl and 55% acetonitrile. Fractions collected from anionic-HPLC were analyzed by ESI. The fraction containing the product (27-29.5 min) was concentrated in Speed-Vac. APDASTREP concentrated solution was quantitated in the final solution using Ni titration method. The copper chelate of the product (Cu-EDTAMP) was prepared and used for further studies.

Example 6

Synthesis of Ciprofloxacin-EDTA (CP-EDTA)

Ciprofloxacin.HCl (MW 367.8) and EDC were from TCI America. EDTA (free acid) was from Aldrich (MW 292.24). All other reagents and solvents were of the highest available purity and used as purchased.

In a glass crimp cap vial with rubber septum, 161 mg EDTA (0.55 mmole) was mixed with 4 mL dry DMSO. The mixture was heated on a hot-plate to complete dissolution of EDTA. After cooling down the solution to RT, 106 mg of EDC (0.55 mmole) was added and mixed at RT for 30 min. Then, 63.3 mg of NHS (0.55 mmole) was added to the mixture and mixed for another 30 min. 184 mg ciprofloxacin.HCl (0.5 mmole) was added to activated EDTA. The vial was wrapped with aluminum foil and the reaction was mixed overnight at RT. A precipitate was formed overnight in the mixture which is soluble in water. The solution was used for HPLC purification.

CP-EDTA was purified by reversed phase HPLC on a C18 column (C18 Semi-prep, 10×250 mm, Vydac). The sample was applied to C18 column and washed for 12 minutes with 20% acetonitrile containing 0.1% TFA (flow rate 1.5 mL/min). A gradient of acetonitrile from 20 to 50% for 30 min resulted in a very good separation of the product (fraction at 27-29 min). The product peak was confirmed be ESI (Negative mode, m/z 604.2, CP-EDTA MW=605.6). The product solution was concentrated in Speed-Vac and quantitated with copper titration. The copper chelate of the product (Cu-CPEDTA) was prepared and used for further studies.

Example 7

Custom peptides were obtained from Genemed Synthesis Inc. or AAPPTEC following synthesis by standard automated peptide synthesis methods and HPLC purification. The chelators 1,4,7,10-tetraazacyclododecane (cyclen) and 1,4,7,10-tetraazacyclododecane-1,4,7,10-tetraacetic acid (DOTA) were obtained from Macrocyclics. Tripeptide GGH-OH (GGH) and tetrapeptide KGHK-OH (SEQ ID NO: 76) (KGHK (SEQ ID NO: 68)) were obtained from Bachem. 1,4,8,11-tetraazacyclotetradecane (cyclam), diethylenetriaminepentaacetic acid (DTPA), nitrilotriacetic acid (NTA), and 1,4,7-triazacyclononane (TACN) were purchased from Sigma. Ethylenediaminetetraacetic acid (EDTA) was purchased from Aldrich. Fe(II) sulfate heptahydrate, Co(II) chloride hexahydrate, Ni(II) tetrahydrate, and Cu(II) chloride dihydrate were purchased from ACROS, J. T.Baker, Aldrich, and J. T. Baker, respectively. Salts, NaCl and NaOH, were purchased from Fisher, and HEPES was purchased from Sigma. Ascorbic acid and rhodamine B were purchased from Fluka. Stabilized 30% hydrogen peroxide solution and dibasic sodium phosphate were purchased from Sigma-Aldrich. TEMPO-9-AC was purchased from Invitrogen.

A peptide incorporating an N-terminal copper binding ATCUN motif and an antimicrobial peptide (AMP) sequence GGHGIRR11RKIIHIIKK-amide (SEQ ID NO: 77) was prepared by automated peptide synthesis and purified by standard HPLC protocols for peptides. Copper was coordinated in solution by addition of aqueous copper ion following HPLC purification. The influence of this compound on cellular oxidative stress was assayed by use of Anaspec Glutathione Cellular Assay Kit Catalog #72158, using drug concentration below the MIC. FIG. 1 shows the significant decrease in concentration of reduced cellular glutathione (−7% to 19%) following addition of Cu-PEP to the medium, relative to the copper free compound.

Example 8

Generation of Reactive Oxygen Species

Figure 4:
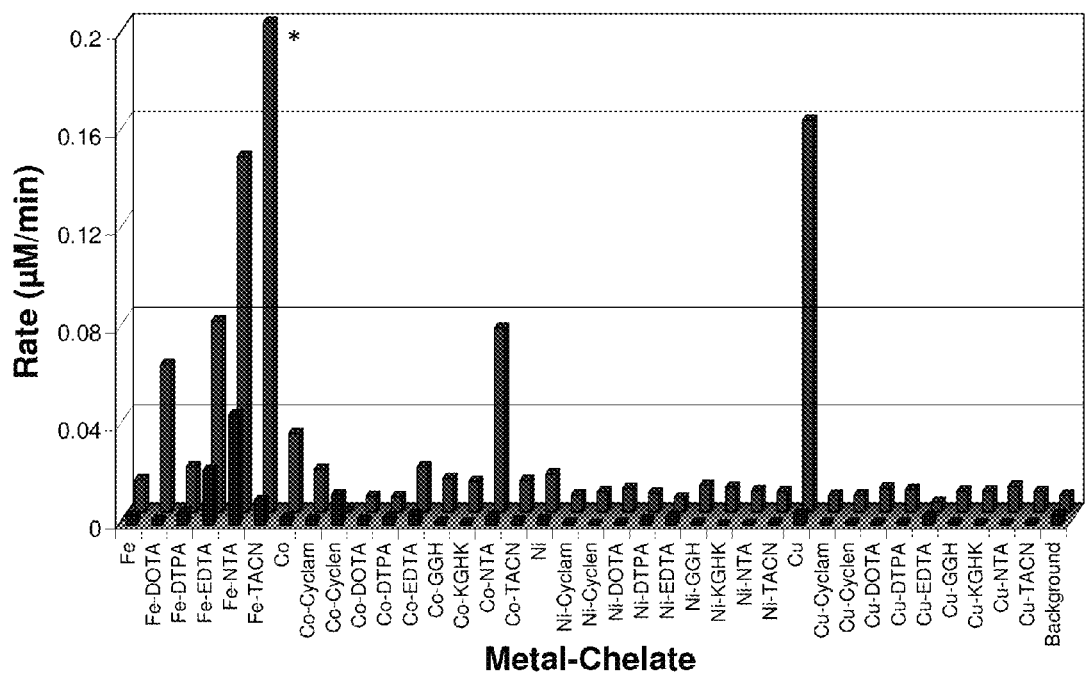
FIG. 4 depicts steady-state rates of TEMPO-9-AC monitored radical generation for each M-chelate/$O_2$ (front bars) and M-chelate/$H_2O_2$ (rear bars) for exemplary compounds of the invention.
Figure 5:
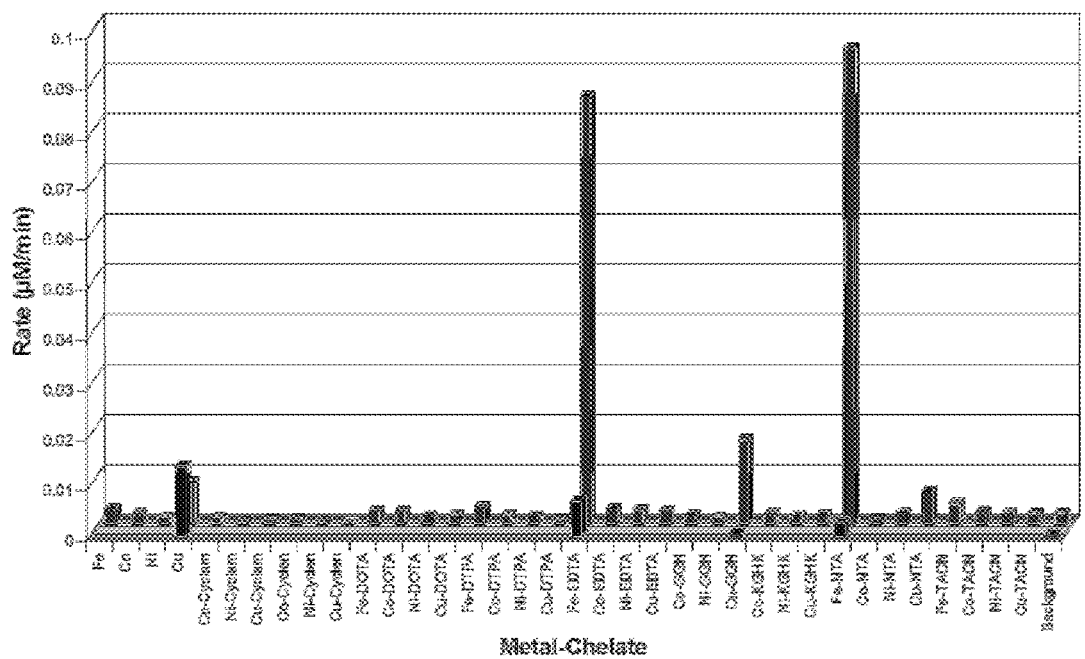
FIG. 5 depicts initial rates for reaction of rhodamine B with each metal-chelate/$O_2$ (front bars) and metal-chelate/$H_2O_2$ (rear bars) for exemplary compounds of the invention.

FIGS. 4 and 5 illustrate the relative rate of production of hydroxyl radical and superoxide species by various metal binding moieties in the presence of ascorbate and peroxide, using tempo and rhodamine to monitor production of such species. The latter are cellular redox species that can react with the metal binding motifs reported herein to produce reactive oxygen species within the cell.

In FIG. 4, steady-state rates of TEMPO-9-AC monitored radical generation for each M-chelate/$O_2$ (front bars) and M-chelate/$H_2O_2$ (rear bars) are depicted. Reactions were run aerobically with 10 μM TEMPO-9-AC and 10 μM M-chelate, with and without 1 mM $H_2O_2$, in 20 mM HEPES, 100 mM NaCl, pH 7.4 in a black-wall 96-well plate. The increase of TEMPO-9-AC fluorescence upon reaction was monitored in real-time by excitation at 358 nm and emission at 435 nm every 4 min on a Varian Cary Eclipse fluorimeter with plate reader attachment. The overall change in fluorescence, which corresponded to the complete reaction of 10 μM TEMPO-9-AC, was used to convert units of fluorescence intensity into units of μM TEMPO-9-AC, and the rates of reaction (μM TEMPO-9-AC/min) were determined from the slopes of the kinetic plots of fluorescence intensity versus time. The Fe-TACN/$H_2O_2$/TEMPO reaction was monitored by stopped-flow techniques due to the extremely high rate. Stopped-flow measurements were made using an Applied Photophysics SpectraKinetic Monochromator, with excitation at 358 nm and an emission filer with band pass >395 nm. Two syringes were used, one containing 20 μM TEMPO-9-AC and 2 mM $H_2O_2$, and the other containing 20 μM Fe-TACN. Data were collected only after two purge injections, and the fitted kinetic trace for the Fe-TACN/$H_2O_2$/TEMPO reaction was the average of 5 trials. * Fe-TACN/$H_2O_2$ in particular was observed to promote very rapid reaction relative to other catalysts, requiring stopped-flow measurements to determine an observed rate of 25.94±0.02 μM/min with the conditions used.

In FIG. 5, initial rates for reaction of rhodamine B with each metal-chelate/$O_2$ (front bars) and metal-chelate/$H_2O_2$ (rear bars) is depicted, reflecting reaction with hydroxyl-radical species generated from the metal redox center. Reactions were run aerobically with 10 μM rhodamine B, 1 mM ascorbate and 1 μM M-chelate, with and without 1 mM H2O2 in 20 mM Na2HPO4, pH 7.4 in a clear 96-well plate. The disappearance of rhodamine B was monitored via UV/Vis at 555 nm on a Molecular Devices SPECTRA MAX M2 plate reader spectrophotometer. The overall change in absorbance, which corresponded to complete reaction of 10 μM RhB, was used to convert units of absorbance into units of μM RhB, and the initial rates (μM RhB/min) were determined from initial slopes of the kinetic plots of absorbance over time.

Example 9

Oxidative stress monitored by protein oxidation and quantitation of protein carbonyls in *E. coli* (ATCC 25922). There is a substantial increase in protein oxidation following exposure of cells to peptide with bound redox active metal, relative to basal levels in the absence of any added reagent, or even after exposure to high concentrations of peroxide.

Formation of Protein Carbonyls in *E. coli* Treated with Either Hydrogen Peroxide or GGHGIRRIIRKIIHIIKK (PEP 188, SEQ ID NO: 16) for 2 hours

| Treatment | Protein Carbonyls (nmol/mg protein) |
|---|---|
| Basal | ND |
| 100 mM $H_2O_2$ | 0.87 |
| 0.375 mM Cu-PEP 188 | 3.50 |

ND—Not detectable

Formation of Protein Carbonyls in *E. coli* Treated with Either Hydrogen Peroxide or GGHGVRRFPWWWPFLRR (PEP 189, SEQ ID NO: 17) for 2 hours

| Treatment | Protein Carbonyls (nmol/mg protein)[a] |
|---|---|
| Basal | ND |
| 100 mM $H_2O_2$ | 0.44 |
| 0.375 mM Cu-PEP 189 | 4.24 |

[a] Average of 2 separate experiments
ND—Not detectable

Figure 6A:
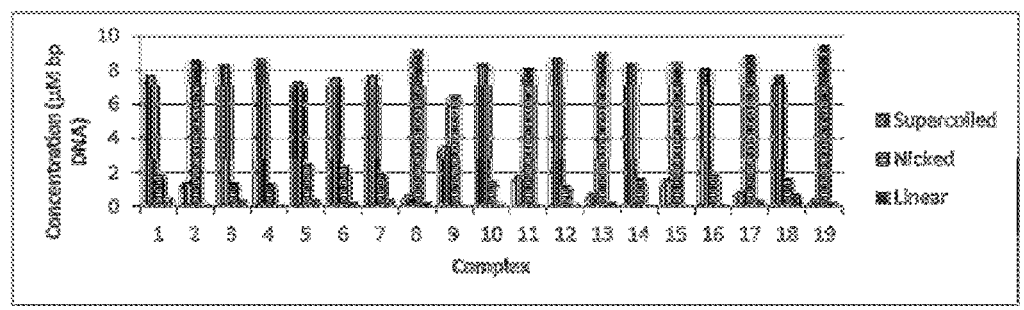
FIGS. 6A and 6B depict oxidative stress monitored by DNA cleavage promoted by reactive oxygen species generated by exemplary compounds of the invention.

Oxidative stress monitored by DNA cleavage promoted by reactive oxygen species generated by the metal-drug is depicted in FIG. 6A. Plasmid DNA was isolated from a pUC19 transformed DH5α *E. coli* cell line and purified by use of a Qiagen miniprep kit following water elution from spin columns (the use of EDTA-containing buffer was avoided). The isolated DNA was quantified by absorbance measurements, divided into single-use aliquots in water, and frozen at −20° C. Ascorbic acid solutions were prepared freshly each day by making a 100 mM ascorbic acid solution in 20 mM HEPES, 100 mM NaCl, and balancing the pH to 7.4 with 1 M NaOH. Ascorbic acid was kept on ice and diluted prior to each experiment. Solutions of $H_2O_2$ were made and used in a similar manner, but without the subsequent pH balancing, since the $H_2O_2$ concentrations used did not alter the pH of the buffer. Stock $H_2O_2$ solutions were freshly prepared from a refrigerated 30% $H_2O_2$ stock and maintained on ice prior to use. The TEMPO-9-AC radical probe was initially dissolved in DMSO and diluted into aliquots in 20 mM HEPES, 100 mM NaCl, pH 7.4. Metal-chelate (M-chelate) complexes were prepared freshly on the day of use by mixing the respective metal salt solution in water with the chelator in buffer to a final ratio of 1:1.5 and incubating for 20-30 min at RT. A slight excess of chelator was added to ensure that no free metal ion was present. Complex formation and chelator concentration were verified by UV/Vis titration. Reactions were run aerobically with 10 μM base pair pUC19, 100 nM M-chelate, 1 mM $H_2O_2$, and 1 mM ascorbate in 20 mM HEPES, 100 mM NaCl, pH 7.4. The reactions were quenched in ice and immediately loaded onto 1% agarose gels containing ethidium bromide, separated for 30-45 min at 120 V, and visualized using a BioRad gel doc. Supercoiled, nicked, and linearized plasmid DNA at each time point was quantified with the program ImageQuant. A correction factor of 1.47 was applied for the intensity of supercoiled DNA to account for the diminished ability of supercoiled DNA to intercalate ethidium bromide.

The following compositions were tested and demonstrate enhanced nicking and linearization of supercoiled DNA by metal-drug complexes that promote formation of reactive oxygen species. Cleavage is enhanced relative to the metal binding moiety itself.

| Composition Number | Complex Name | Supercoiled (μM bp) | Nicked (μM bp) | Linear (μM bp) |
|---|---|---|---|---|
| 1 | None | 7.71 | 1.85 | 0.43 |
| 2 | Cu-GGH | 1.34 | 8.53 | 0.13 |
| 3 | Fe-DOTA | 8.32 | 1.35 | 0.33 |
| 4 | Cu-DOTA | 8.59 | 1.31 | 0.09 |
| 5 | Fe-EDTA | 7.26 | 2.44 | 0.30 |
| 6 | Cu-EDTA | 7.50 | 2.29 | 0.21 |
| 7 | free Fe | 7.71 | 1.91 | 0.38 |
| 8 | free Cu | 0.63 | 9.16 | 0.21 |
| 9 | Cu-GGHC-Amik fr3 (SEQ ID NO: 78) | 3.50 | 6.46 | 0.04 |
| 10 | Fe-EDTA-Amp | 8.35 | 1.50 | 0.15 |
| 11 | Cu-EDTA-Amp | 1.79 | 8.09 | 0.12 |
| 12 | Fe-EDTA-Amox | 8.65 | 1.19 | 0.17 |
| 13 | Cu-EDTA-Amox | 0.77 | 9.01 | 0.22 |
| 14 | Fe-hEDTA-Amox | 8.37 | 1.59 | 0.03 |
| 15 | Cu-hEDTA-Amox | 1.52 | 8.44 | 0.04 |
| 16 | Fe-EDTA-ACA | 8.06 | 1.85 | 0.09 |
| 17 | Cu-EDTA-ACA | 0.82 | 8.85 | 0.32 |
| 18 | Fe-EDTA(ACA)2 | 7.71 | 1.61 | 0.68 |
| 19 | Cu-EDTA(ACA)2 | 0.36 | 9.41 | 0.23 |

Example 10

Figure 6B:
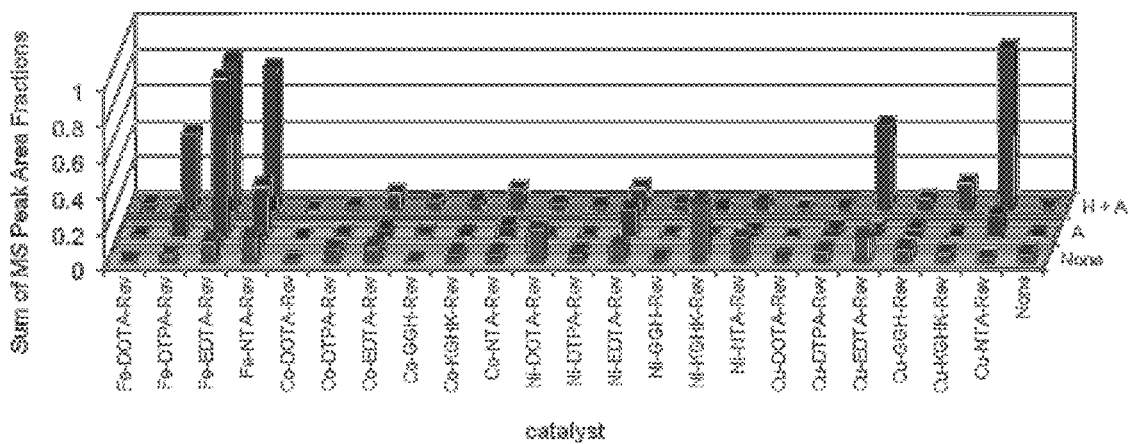

Catalyst-mediated cleavage of an RNA was observed both under oxidative conditions (in the presence of 1 mM of ascorbate, A, and/or peroxide, H), or under hydrolytic conditions in the absence of redox coreagents (none) as depicted in FIG. 6B. Reactions of 10 μM catalyst, 1 mM co-reactants (ascorbate, $H_2O_2$, and/or no co-reactants), and 10 μM RNA were conducted at 37° C. in separate tubes, each containing 20 μL total reaction volume. A reaction buffer consisting of 20 mM HEPES, 100 mM NaCl, pH 7.4 was used in all experiments. Prior to reaction, RNA was heated to 90° C. for 5 min and allowed to cool to 37° C., and the RNA was immediately added to each pre-incubated tube. For time-dependent reactions, one tube corresponded to one time point, with staggering of start times and quenching of all reactions at the same time. To initiate reactions, catalyst and co-reactants were mixed with pre-incubated RNA, and reactions were performed in a dark incubator. Reactions were quenched by placement on ice and immediately desalted using C18 ziptips, and eluted in 50/50 acetonitrile/water.

Example 11

Minimal Inhibitory Concentrations (MIC's, μM) for metallodrugs were determined against various bacteria. The metallodrugs of the present invention can be offered with a metal bound at the time of administration, or in metal free form in which case the composition likely recruits metal from the medium. The following compositions were tested:

```
SEQ ID NO: 13:  PEP 35    GGHTRQARRNRRRWRERQR

SEQ ID NO: 14:  PEP 36    KGHKTRQARRNRRRWRERQR

SEQ ID NO: 15:  PEP 142   GGHTRSSRAGLQFPVGRVHRLLRK

SEQ ID NO: 16:  PEP 188   GGHGIRRIIRKIIHIIKK

SEQ ID NO: 17:  PEP 189   GGHGVRRFPWWWPFLRR

-continued
SEQ ID NO: 18:  PEP 190   GGHGILAWKWAWWAWRR

SEQ ID NO: 19:  PEP 191   GGHGRLARIVVIRVAR

SEQ ID NO: 20:  PEP 192   GGHGQRKLFFNLRKTKQRLGWFNQC

SEQ ID NO: 21:  PEP 193   GGHGEYVLRNWRIVKVATTKAC

SEQ ID NO: 22:  PEP 201   GGHGHPVHHYQ

SEQ ID NO: 23:  PEP 202   GGHGGHPVHHYQ

SEQ ID NO: 24:  PEP 203   GGHGLPLTPLP

SEQ ID NO: 25:  PEP 204   GGHGWRWYCR

SEQ ID NO: 26:  PEP 205   GGHTRQARRNRR

SEQ ID NO: 27:  PEP 231   GGHGLFDIIKKIAESI

SEQ ID NO: 28:  PEP 234   GGHFLPLIGRVLSGIL

SEQ ID NO: 29:  PEP 242   GGHFVQWFSKFLGRIL

SEQ ID NO: 30:  PEP 245   GGHGWRTLLKKAEVKTVGKLALKHYL

SEQ ID NO: 31:  PEP 250   GGHKGRGKQGGKVRAKAKTRSS

SEQ ID NO: 32:  PEP 256   GGHILPWKWPWWPWRR

SEQ ID NO: 33:  PEP 257   GGHVRRFPWWWPFLRR

SEQ ID NO: 34:  PEP 263   GGHFKCRRWQWRMKKLGAPSITCVRRAF

SEQ ID NO: 35:  PEP 267   GGHGIGKFLHSAGKFGKAFVGEIMKS

SEQ ID NO: 36:  PEP 271   GGHVDKGSYLPRPTPPRPIYNRN

SEQ ID NO: 37:  PEP 311   GGHGIRRIIRKIIHIIKKGGC

SEQ ID NO: 38:  PEP 312   GGHGVRRFPWWWPFLRRGGC

SEQ ID NO: 39:  PEP 313   GGHGILAWKWAWWAWRRGGC

SEQ ID NO: 40:  PEP 314   GGHRRWKIVVIRWRRGGC

SEQ ID NO: 41:  PEP 315   GGHFVQWFSKFLGRILGGC

SEQ ID NO: 42:  PEP 316   GGHILPWKWPWWPWRRGGC

SEQ ID NO: 43:  PEP 318   GGHIRRIIRKIIHIIKKGGC

SEQ ID NO: 44:  PEP 319   GGHVRRFPWWWPFLRRGGC

SEQ ID NO: 45:  PEP 321   GGHGRRWKIVVIRWRRGGC

SEQ ID NO: 46:  PEP 322   GGHWRWYCRGGK

SEQ ID NO: 47:  PEP 323   GGHGWRWYCRGGK

SEQ ID NO: 48:  NTA-Rev   NTATRQARRNRRRRWRERQR

SEQ ID NO: 49:  EDTA-Rev  EDTATRQARRNRRRRWRERQR

SEQ ID NO: 50:  DOTA-Rev  DOTATRQARRNRRRRWRERQR

SEQ ID NO: 51:  DTPA-Rev  DTPATRQARRNRRRRWRERQR
```

Bacteria for testing were obtained from ATCC and the following strains were used (Ec, *E. coli*, 25922; Ec F, *E. coli* O157:H7, BAA-1883; Se, *S. enteric*, 6539; MRSA, 43300; P. aeuginosa, 27583; Kp, *K. pneumonia*, 700603; Sa, *S. aureus*, 29213; Ef, *E. faecium*, 700221; Ab, *A. baumanii*, BAA-747; Hi, *H. influenzae*, 49247; Sp, *S. pneumoniae*, 49619; Bc, *B. cepacia*, 25416;). Bacterial minimal inhibitory concentrations (MIC's) for the various test articles were determined by standard solution broth methods [Wiegand, I. et al. Nat. Protocols 3(2):163-168 (2008); Andrews, J. M. J. Antimicob. Chemother. 48(Suppl. S1):5-16 (2001); Koeth, L. M. Int. J. Antimicrob. Agents 23:17-24 (2004)] using Mueller Hinton Broth (Difco; Catalog No. 275730). All MIC values are expressed in units of µM.

| | Ec | | Se | | Ef | | Ab | | Hi |
|---|---|---|---|---|---|---|---|---|---|
| DOTAMP | 42.5 | GGHCAMIK (SEQ ID NO: 79) | 16.7 | GGH CIPRO | 4 | PEP 188 | 0.9 | PEP 305 | 4 |
| PEP 188 | 1.9 | DOTAMP | 10.6 | PEP 188 | 0.9 | PEP 189 | 3.8 | PEP 311 | 31.7 |
| PEP 189 | 1.8 | GGH CIPRO | 16 | PEP 189 | 1.8 | PEP 190 | 3.7 | PEP 314 | 3.7 |
| PEP 190 | 15 | PEP 188 | 0.9 | PEP 190 | 3.7 | PEP 191 | 9.3 | PEP316 | 13.5 |
| PEP 191 | 2.3 | PEP 189 | 7.2 | PEP 191 | 18.5 | PEP 204 | 25.1 | PEP 321 | 14.2 |
| PEP 192 | 5.3 | PEP 190 | 15 | PEP 192 | 10.6 | PEP 311 | 2 | PEP 322 | 2.7 |
| PEP 204 | 3.1 | PEP 191 | 37 | PEP 204 | 25.1 | PEP 314 | 7.3 | PEP 323 | 1.5 |
| PEP 305 | 66.1 | PEP 192 | 10.6 | PEP 305 | 8.2 | PEP 321 | 28.4 | PEP 318 PEG 12 | 2.7 |
| PEP 311 | 7.9 | PEP 204 | 6.3 | PEP 311 | 4 | PEP 322 | 21.9 | | |
| PEP 314 | 14.6 | PEP 305 | 8.2 | PEP 314 | 3.7 | PEP 323 | 20.9 | | Sp |
| PEP 322 | 21.9 | PEP 314 | 3.7 | PEP316 | 3.4 | PEP 318 | 7 | PEP 188 | 3.8 |
| PEP 323 | 20.9 | PEP 321 | 7.1 | PEP 321 | 7.1 | PEP 314 PEG 12 | 2.7 | PEP 189 | 7.2 |
| PEP 318 | 7 | PEP 322 | 2.7 | PEP 322 | 2.7 | PEP 318 PEG 12 | 5.4 | PEP 190 | 15 |
| PEP 314 PEG 12 | 11 | PEP 323 | 5.3 | PEP 323 | 5.3 | PEG 318 PEP 24 | 9.1 | PEP 191 | 37 |
| PEP 318 PEG 12 | 10.7 | PEP 318 | 3.5 | PEP 312 | 3.3 | PEP 318 PEG 36 | 7.9 | PEP 305 | 0.5 |
| PEP 318 PEG 24 | 9.1 | PEP 314 PEG 12 | 5.5 | PEP 313 | 6.8 | PEP 318 PEG 48 | 13.9 | PEP 311 | 15.8 |
| PEP 318 PEG 36 | 15.8 | PEP 314 PEG 24 | 9.3 | PEP 318 | 3.5 | | | PEP 314 | 0.9 |
| | | PEP 318 PEG 12 | 5.4 | PEP 319 | 3.4 | | Sa | PEP316 | 0.8 |
| | Ec F | PEP 318 PEG 24 | 4.6 | PEP 314 PEG 12 | 11 | PEP 192 | 10.6 | PEP 321 | 1.8 |
| DOTAMP | 42.5 | PEP 318 PEG 36 | 7.9 | PEP 314 PEG 24 | 4.7 | PEP 305 | 33.1 | PEP 322 | 0.3 |
| GGH CIPRO | 8 | PEP 318 PEG 48 | 7 | PEP 314 PEG 36 | 4 | PEP 311 | 7.9 | PEP 323 | 0.16 |
| PEP 188 | 3.8 | | | PEP 314 PEG 48 | 3.6 | PEP 314 | 29.2 | PEP 312 | 3.3 |
| PEP 189 | 7.2 | | MRSA | PEP 318 PEG 12 | 21.4 | PEP 322 | 43.8 | PEP 313 | 6.8 |
| PEP 190 | 15 | DOTAMP | 42.5 | PEP 318 PEG 24 | 9.1 | PEP 323 | 42 | PEP 318 | 3.5 |
| PEP 191 | 37 | GGH CIPRO | 32 | PEP 318 PEG 36 | 15.8 | PEP 318 | 14.1 | PEP 319 | 1.7 |
| PEP 204 | 50 | PEP 188 | 0.9 | | | | | PEP 314 PEG 12 | 11 |
| PEP 305 | 8.2 | PEP 189 | 1.8 | | Pa | | Kp | PEP 314 PEG 24 | 4.7 |
| PEP 311 | 4 | PEP 191 | 1.2 | PEP 188 | 1.9 | PEP 188 | 1.9 | PEP 314 PEG 36 | 8.1 |
| PEP 314 | 7.3 | PEP 192 | 10.6 | PEP 189 | 7.2 | PEP 189 | 7.2 | PEP 314 PEG 48 | 7.1 |
| PEP 321 | 14.2 | PEP 193 | 13 | PEP 191 | 18.5 | PEP 192 | 5.3 | PEP 318 PEG 12 | 5.4 |
| PEP 322 | 2.7 | PEP 204 | 6.3 | PEP 192 | 10.6 | PEP 204 | 4.7 | | |
| PEP 323 | 5.3 | PEP 205 | 21.9 | PEP 204 | 25 | PEP 305 | 66.1 | | Bc |
| PEP 318 ov-3 | 3.5 | PEP 305 | 33.1 | PEP 205 | 43.7 | PEP 311 | 7.9 | PEP 318 PEG 12 | 2.7 |
| PEP 314 PEG 12 | 11 | PEP 314 | 14.6 | PEP 305 | 66.1 | PEP 314 | 14.6 | | |
| PEP 314 PEG 24 | 9.3 | PEP 321 | 14.2 | PEP 311 | 15.8 | PEP 321 | 14.2 | | |
| PEP 318 PEG 12 | 5.4 | PEP 322 | 7.6 | PEP 314 | 14.6 | PEP 322 | 7.6 | | |
| PEP 318 PEG 24 | 18.2 | PEP 323 | 20.9 | PEP 322 | 21.9 | PEP 323 | 20.9 | | |
| PEP 318 PEG 36 | 15.8 | PEP 318 | 14.1 | PEP 323 | 20.9 | PEP 318 | 28.2 | | |
| | | PEP 314 PEG 12 | 22 | PEP 318 | 28.2 | PEP 318 PEG 12 | 21.4 | | |
| | | PEP 314 PEG 24 | 18.7 | | | | | | |

To understand the effect or pegylation on the claimed compositions, PEP314 and PEP318 were pegylated with PEG24, PEG36, and PEG48, where the numbers 24, 36, and 48 indicate the number of ethylene glycol units in the PEG molecule. PEG conjugation was performed at cysteine or lysine side chains in the peptides using N-ethyl maleimide or N-hydroxysuccinimide crosslinking reagents. As shown in the following table, pegylation of antimicrobial peptides (with and without a metal-binding domain) and in metal-bound and metal-free forms for antimicrobial peptides possessing a metal-binding domain, can be used to reduce the IC50 for cytotoxicity toward human Huh7 liver cells.

| Compound | IC50 μM |
|---|---|
| PEP 314 | 17 |
| PEP 314 PEG 24 | nt |
| PEP 314 PEG 36 | nt |
| PEP 314 PEG 48 | n

```
<213> ORGANISM: Unknown
<220> FEATURE:
<223> OTHER INFORMATION: Description of Unknown: Alpha-helical peptide

<400> SEQUENCE: 3

Phe Val Gln Trp Phe Ser Lys Phe Leu Gly Arg Ile Leu
1               5                   10

<210> SEQ ID NO 4
<211> LENGTH: 14
<212> TYPE: PRT
<213> ORGANISM: Unknown
<220> FEATURE:
<223> OTHER INFORMATION: Description of Unknown: Alpha-helical peptide

<400> SEQUENCE: 4

Ile Arg Arg Ile Ile Arg Lys Ile Ile His Ile Ile Lys Lys
1               5                   10

<210> SEQ ID NO 5
<211> LENGTH: 13
<212> TYPE: PRT
<213> ORGANISM: Unknown
<220> FEATURE:
<223> OTHER INFORMATION: Description of Unknown: Alpha-helical peptide

<400> SEQUENCE: 5

Ile Leu Ala Trp Lys Trp Ala Trp Trp Ala Trp Arg Arg
1               5                   10

<210> SEQ ID NO 6
<211> LENGTH: 23
<212> TYPE: PRT
<213> ORGANISM: Unknown
<220> FEATURE:
<223> OTHER INFORMATION: Description of Unknown: Alpha-helical peptide

<400> SEQUENCE: 6

Gly Trp Arg Thr Leu Leu Lys Lys Ala Glu Val Lys Thr Val Gly Lys
1               5                   10                  15

Leu Ala Leu Lys His Tyr Leu
            20

<210> SEQ ID NO 7
<211> LENGTH: 19
<212> TYPE: PRT
<213> ORGANISM: Unknown
<220> FEATURE:
<223> OTHER INFORMATION: Description of Unknown: Alpha-helical peptide

<400> SEQUENCE: 7

Lys Gly Arg Gly Lys Gln Gly Gly Lys Val Arg Ala Lys Ala Lys Thr
1               5                   10                  15

Arg Ser Ser

<210> SEQ ID NO 8
<211> LENGTH: 17
<212> TYPE: PRT
<213> ORGANISM: Unknown
<220> FEATURE:
<223> OTHER INFORMATION: Description of Unknown: Beta-sheet peptide

<400> SEQUENCE: 8

Trp Asn Leu Leu Arg Gln Ala Gln Glu Lys Phe Gly Lys Asp Lys Ser
1               5                   10                  15
```

Pro

<210> SEQ ID NO 9
<211> LENGTH: 25
<212> TYPE: PRT
<213> ORGANISM: Unknown
<220> FEATURE:
<223> OTHER INFORMATION: Description of Unknown: Beta-sheet peptide

<400> SEQUENCE: 9

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 10
<211> LENGTH: 20
<212> TYPE: PRT
<213> ORGANISM: Unknown
<220> FEATURE:
<223> OTHER INFORMATION: Description of Unknown: Beta-sheet peptide

<400> SEQUENCE: 10

Val Asp Lys Gly Ser Tyr Leu Pro Arg Pro Thr Pro Pro Arg Pro Ile
1               5                   10                  15

Tyr Asn Arg Asn
            20

<210> SEQ ID NO 11
<211> LENGTH: 13
<212> TYPE: PRT
<213> ORGANISM: Unknown
<220> FEATURE:
<223> OTHER INFORMATION: Description of Unknown: Extended backbone
      peptide

<400> SEQUENCE: 11

Ile Leu Pro Trp Lys Trp Pro Trp Trp Pro Trp Arg Arg
1               5                   10

<210> SEQ ID NO 12
<211> LENGTH: 25
<212> TYPE: PRT
<213> ORGANISM: Unknown
<220> FEATURE:
<223> OTHER INFORMATION: Description of Unknown: Ring peptide

<400> SEQUENCE: 12

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly His Thr Arg Gln Ala Arg Arg Asn Arg Arg Arg Arg Trp Arg
1               5                   10                  15

Glu Arg Gln Arg

```
         20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Gly His Lys Thr Arg Gln Ala Arg Arg Asn Arg Arg Arg Arg Trp
1               5                   10                  15

Arg Glu Arg Gln Arg
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly His Thr Arg Ser Ser Arg Ala Gly Leu Gln Phe Pro Val Gly
1               5                   10                  15

Arg Val His Arg Leu Leu Arg Lys
            20

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly His Gly Ile Arg Arg Ile Ile Arg Lys Ile Ile His Ile Ile
1               5                   10                  15

Lys Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly His Gly Val Arg Arg Phe Pro Trp Trp Trp Pro Phe Leu Arg
1               5                   10                  15

Arg

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Gly Gly His Gly Ile Leu Ala Trp Lys Trp Ala Trp Trp Ala Trp Arg
1               5                   10                  15

Arg
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gly Gly His Gly Arg Leu Ala Arg Ile Val Val Ile Arg Val Ala Arg
1               5                   10                  15
```

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gly Gly His Gly Gln Arg Lys Leu Phe Phe Asn Leu Arg Lys Thr Lys
1               5                   10                  15

Gln Arg Leu Gly Trp Phe Asn Gln Cys
            20                  25
```

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Gly Gly His Gly Glu Tyr Val Leu Arg Asn Trp Arg Ile Val Lys Val
1               5                   10                  15

Ala Thr Thr Lys Ala Cys
            20
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gly Gly His Gly His Pro Val His His Tyr Gln
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gly Gly His Gly Gly His Pro Val His His Tyr Gln
```

```
<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly His Gly Leu Pro Leu Thr Pro Leu Pro
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly His Gly Trp Arg Trp Tyr Cys Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly His Thr Arg Gln Ala Arg Arg Asn Arg Arg
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly His Gly Leu Phe Asp Ile Ile Lys Lys Ile Ala Glu Ser Ile
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly His Phe Leu Pro Leu Ile Gly Arg Val Leu Ser Gly Ile Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 29

Gly Gly His Phe Val Gln Trp Phe Ser Lys Phe Leu Gly Arg Ile Leu
1               5                   10                  15

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly His Gly Trp Arg Thr Leu Leu Lys Lys Ala Glu Val Lys Thr
1               5                   10                  15

Val Gly Lys Leu Ala Leu Lys His Tyr Leu
            20                  25

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly His Lys Gly Arg Gly Lys Gln Gly Gly Lys Val Arg Ala Lys
1               5                   10                  15

Ala Lys Thr Arg Ser Ser
            20

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly His Ile Leu Pro Trp Lys Trp Pro Trp Trp Pro Trp Arg Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly His Val Arg Arg Phe Pro Trp Trp Trp Pro Phe Leu Arg Arg
1               5                   10                  15

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Gly Gly His Phe Lys Cys Arg Arg Trp Gln Trp Arg Met Lys Leu
1               5                   10                  15

Gly Ala Pro Ser Ile Thr Cys Val Arg Arg Ala Phe
            20                  25

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly His Gly Ile Gly Lys Phe Leu His Ser Ala Gly Lys Phe Gly
1               5                   10                  15

Lys Ala Phe Val Gly Glu Ile Met Lys Ser
            20                  25

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly His Val Asp Lys Gly Ser Tyr Leu Pro Arg Pro Thr Pro Pro
1               5                   10                  15

Arg Pro Ile Tyr Asn Arg Asn
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly His Gly Ile Arg Arg Ile Ile Arg Lys Ile Ile His Ile Ile
1               5                   10                  15

Lys Lys Gly Gly Cys
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly His Gly Val Arg Arg Phe Pro Trp Trp Trp Pro Phe Leu Arg
1               5                   10                  15

Arg Gly Gly Cys
            20

<210> SEQ ID NO 39
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 39

Gly Gly His Gly Ile Leu Ala Trp Lys Trp Ala Trp Trp Ala Trp Arg
1               5                   10                  15

Arg Gly Gly Cys
            20

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly His Arg Arg Trp Lys Ile Val Val Ile Arg Trp Arg Arg Gly
1               5                   10                  15

Gly Cys

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly His Phe Val Gln Trp Phe Ser Lys Phe Leu Gly Arg Ile Leu
1               5                   10                  15

Gly Gly Cys

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly His Ile Leu Pro Trp Lys Trp Pro Trp Trp Pro Trp Arg Arg
1               5                   10                  15

Gly Gly Cys

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly His Ile Arg Arg Ile Ile Arg Lys Ile His Ile Ile Lys
1               5                   10                  15

Lys Gly Gly Cys
            20
```

```
<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly His Val Arg Arg Phe Pro Trp Trp Pro Phe Leu Arg Arg
1               5                   10                  15

Gly Gly Cys

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly His Gly Arg Arg Trp Lys Ile Val Val Ile Arg Trp Arg Arg
1               5                   10                  15

Gly Gly Cys

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly His Trp Arg Trp Tyr Cys Arg Gly Gly Lys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly His Gly Trp Arg Trp Tyr Cys Arg Gly Gly Lys
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NTA

<400> SEQUENCE: 48

Thr Arg Gln Ala Arg Arg Asn Arg Arg Arg Trp Arg Glu Arg Gln
1               5                   10                  15

Arg

<210> SEQ ID NO 49
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term EDTA

<400> SEQUENCE: 49

Thr Arg Gln Ala Arg Arg Asn Arg Arg Arg Arg Trp Arg Glu Arg Gln
1               5                   10                  15

Arg

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA

<400> SEQUENCE: 50

Thr Arg Gln Ala Arg Arg Asn Arg Arg Arg Arg Trp Arg Glu Arg Gln
1               5                   10                  15

Arg

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DTPA

<400> SEQUENCE: 51

Thr Arg Gln Ala Arg Arg Asn Arg Arg Arg Arg Trp Arg Glu Arg Gln
1               5                   10                  15

Arg

<210> SEQ ID NO 52
<211> LENGTH: 21
<212> TYPE: PRT
<213> ORGANISM: Unknown
<220> FEATURE:
<223> OTHER INFORMATION: Description of Unknown: Antimicrobial peptide

<400> SEQUENCE: 52

Thr Arg Ser Ser Arg Ala Gly Leu Gln Phe Pro Val Gly Arg Val His
1               5                   10                  15

Arg Leu Leu Arg Lys
            20

<210> SEQ ID NO 53
<211> LENGTH: 15
<212> TYPE: PRT
<213> ORGANISM: Unknown
<220> FEATURE:
<223> OTHER INFORMATION: Description of Unknown: Antimicrobial peptide

<400> SEQUENCE: 53

Gly Ile Arg Arg Ile Ile Arg Lys Ile Ile His Ile Ile Lys Lys
```

```
                1               5                   10                  15
```

<210> SEQ ID NO 54
<211> LENGTH: 14
<212> TYPE: PRT
<213> ORGANISM: Unknown
<220> FEATURE:
<223> OTHER INFORMATION: Description of Unknown: Antimicrobial peptide

<400> SEQUENCE: 54

```
Gly Val Arg Arg Phe Pro Trp Trp Trp Pro Phe Leu Arg Arg
1               5                   10
```

<210> SEQ ID NO 55
<211> LENGTH: 14
<212> TYPE: PRT
<213> ORGANISM: Unknown
<220> FEATURE:
<223> OTHER INFORMATION: Description of Unknown: Antimicrobial peptide

<400> SEQUENCE: 55

```
Gly Ile Leu Ala Trp Lys Trp Ala Trp Trp Ala Trp Arg Arg
1               5                   10
```

<210> SEQ ID NO 56
<211> LENGTH: 13
<212> TYPE: PRT
<213> ORGANISM: Unknown
<220> FEATURE:
<223> OTHER INFORMATION: Description of Unknown: Antimicrobial peptide

<400> SEQUENCE: 56

```
Gly Arg Leu Ala Arg Ile Val Val Ile Arg Val Ala Arg
1               5                   10
```

<210> SEQ ID NO 57
<211> LENGTH: 23
<212> TYPE: PRT
<213> ORGANISM: Unknown
<220> FEATURE:
<223> OTHER INFORMATION: Description of Unknown: Antimicrobial peptide

<400> SEQUENCE: 57

```
Gly Ile Gly Lys Phe Leu His Ser Ala Gly Lys Phe Gly Lys Ala Phe
1               5                   10                  15

Val Gly Glu Ile Met Lys Ser
            20
```

<210> SEQ ID NO 58
<211> LENGTH: 20
<212> TYPE: PRT
<213> ORGANISM: Unknown
<220> FEATURE:
<223> OTHER INFORMATION: Description of Unknown: Antimicrobial peptide

<400> SEQUENCE: 58

```
Val Asp Lys Gly Ser Tyr Leu Pro Arg Pro Thr Pro Pro Arg Pro Ile
1               5                   10                  15

Tyr Asn Arg Asn
            20
```

<210> SEQ ID NO 59
<211> LENGTH: 18
<212> TYPE: PRT
<213> ORGANISM: Unknown
<220> FEATURE:

<223> OTHER INFORMATION: Description of Unknown: Antimicrobial peptide

<400> SEQUENCE: 59

Gly Ile Arg Arg Ile Ile Arg Lys Ile Ile His Ile Ile Lys Lys Gly
1               5                   10                  15

Gly Cys

<210> SEQ ID NO 60
<211> LENGTH: 14
<212> TYPE: PRT
<213> ORGANISM: Unknown
<220> FEATURE:
<223> OTHER INFORMATION: Description of Unknown: Antimicrobial peptide

<400> SEQUENCE: 60

Arg Phe Pro Trp Trp Trp Pro Phe Leu Arg Arg Gly Gly Cys
1               5                   10

<210> SEQ ID NO 61
<211> LENGTH: 17
<212> TYPE: PRT
<213> ORGANISM: Unknown
<220> FEATURE:
<223> OTHER INFORMATION: Description of Unknown: Antimicrobial peptide

<400> SEQUENCE: 61

Gly Ile Leu Ala Trp Lys Trp Ala Trp Trp Ala Trp Arg Arg Gly Gly
1               5                   10                  15

Cys

<210> SEQ ID NO 62
<211> LENGTH: 15
<212> TYPE: PRT
<213> ORGANISM: Unknown
<220> FEATURE:
<223> OTHER INFORMATION: Description of Unknown: Antimicrobial peptide

<400> SEQUENCE: 62

Arg Arg Trp Lys Ile Val Val Ile Arg Trp Arg Arg Gly Gly Cys
1               5                   10                  15

<210> SEQ ID NO 63
<211> LENGTH: 16
<212> TYPE: PRT
<213> ORGANISM: Unknown
<220> FEATURE:
<223> OTHER INFORMATION: Description of Unknown: Antimicrobial peptide

<400> SEQUENCE: 63

Phe Val Gln Trp Phe Ser Lys Phe Leu Gly Arg Ile Leu Gly Gly Cys
1               5                   10                  15

<210> SEQ ID NO 64
<211> LENGTH: 16
<212> TYPE: PRT
<213> ORGANISM: Unknown
<220> FEATURE:
<223> OTHER INFORMATION: Description of Unknown: Antimicrobial peptide

<400> SEQUENCE: 64

Ile Leu Pro Trp Lys Trp Pro Trp Trp Pro Trp Arg Arg Gly Gly Cys
1               5                   10                  15

<210> SEQ ID NO 65
<211> LENGTH: 17

```
<212> TYPE: PRT
<213> ORGANISM: Unknown
<220> FEATURE:
<223> OTHER INFORMATION: Description of Unknown: Antimicrobial peptide

<400> SEQUENCE: 65

Ile Arg Arg Ile Ile Arg Lys Ile Ile His Ile Ile Lys Lys Gly Gly
1               5                   10                  15
Cys

<210> SEQ ID NO 66
<211> LENGTH: 16
<212> TYPE: PRT
<213> ORGANISM: Unknown
<220> FEATURE:
<223> OTHER INFORMATION: Description of Unknown: Antimicrobial peptide

<400> SEQUENCE: 66

Val Arg Arg Phe Pro Trp Trp Trp Pro Phe Leu Arg Arg Gly Gly Cys
1               5                   10                  15

<210> SEQ ID NO 67
<211> LENGTH: 16
<212> TYPE: PRT
<213> ORGANISM: Unknown
<220> FEATURE:
<223> OTHER INFORMATION: Description of Unknown: Antimicrobial peptide

<400> SEQUENCE: 67

Gly Arg Arg Trp Lys Ile Val Val Ile Arg Trp Arg Arg Gly Gly Cys
1               5                   10                  15

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly His Lys
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Ile His Asn
1

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile His Pro Phe
1               5
```

```
<210> SEQ ID NO 71
<211> LENGTH: 8
<212> TYPE: PRT
<213> ORGANISM: Unknown
<220> FEATURE:
<223> OTHER INFORMATION: Description of Unknown: Prion protein peptide

<400> SEQUENCE: 71

Pro His Gly Gly Gly Trp Gly Gln
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Gly Gly Gly
1

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

His Gly Gly Gly Gly
1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

His Gly Gly Cys
1

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Tyr Ala Cys Ala Ala Cys Ala Ala Ala Phe Ala Ala Lys Ala Ala
1               5                   10                  15

Leu Ala Ala His Ala Ala Ala His Ala Lys
            20                  25

<210> SEQ ID NO 76
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: C-term OH

<400> SEQUENCE: 76

Lys Gly His Lys
1

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 77

Gly Gly His Gly Ile Arg Arg Ile Ile Arg Lys Ile Ile His Ile Ile
1               5                   10                  15

Lys Lys

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term Amik

<400> SEQUENCE: 78

Gly Gly His Cys
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term Amik

<400> SEQUENCE: 79

Gly Gly His Cys
1

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term amide

<400> SEQUENCE: 80

Gly Gly His Gly Ile Arg Arg Ile Ile Arg Lys Ile Ile His Ile Ile
1               5                   10                  15
```

```
Lys Lys

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Co

<400> SEQUENCE: 81

Lys Gly His Lys
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ni

<400> SEQUENCE: 82

Lys Gly His Lys
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 83

Lys Gly His Lys
1
```

We claim:

1. An antimicrobial composition, comprising:
   a first moiety which is (i) an antimicrobial peptide ("AMP"), or peptide that binds to a pathogenic target, the sequence of which is between 6 and 100 amino acids, is net positively charged, and is amphipathic, (ii) an antibiotic, or (iii) a conjugate comprising an AMP, or peptide that binds to a pathogenic target, and an antibiotic; and
   a second moiety which is a metal binding moiety selected from the group consisting of a peptide motif, a cyclam, a cyclen, and a non-porphyrin macrocyclic chelating agent,
   wherein the first moiety and the second moiety are covalently linked to form a complex, wherein the second moiety is heterologous to the first moiety, wherein the first moiety and the second moiety act separately, with distinct functions, in such a way that the second moiety enhances the antimicrobial effects of the first moiety, and wherein the first moiety promotes uptake of the complex into a target cell or organelle.

2. The composition according to claim 1, wherein the first moiety comprises an antimicrobial peptide, or peptide that binds to a pathogenic target, that adopts a structure selected from the group consisting of an α-helix, a β-hairpin-like beta-sheet, a beta-sheet, or an α-helix/beta-sheet mixed structure.

3. The composition according to claim 2, wherein the antimicrobial peptide, or peptide that binds to a pathogenic target, adopts an amphipathic α-helical structure.

4. The composition according to claim 2, wherein the antimicrobial peptide, or peptide that binds to a pathogenic target, adopts a structure comprising antiparallel β-sheets.

5. The composition according to claim 2, wherein the antimicrobial peptide, or peptide that binds to a pathogenic target, adopts an extended backbone structure.

6. The composition according to claim 2, wherein the antimicrobial peptide, or peptide that binds to a pathogenic target, adopts a ring structure.

7. The composition according to claim 1, wherein the metal binding moiety comprises a metal bound thereto, wherein said metal is redox-active in the bound state under oxidative conditions to generate one or more reactive oxygen species.

8. The composition according to claim 1, wherein the metal binding moiety has a metal bound thereto, wherein said metal is active as a Lewis acid catalyst in the bound state under hydrolytic conditions.

9. The composition according to claim 1, wherein the metal binding moiety comprises a metal bound thereto, wherein said metal is a cation of a metal selected from the group consisting of alkaline earth metals, metals which give rise to cations with an incomplete d sub-shell, lanthanide and actinide metals.

10. The composition according to claim 1, wherein the metal binding moiety comprises a transition metal bound thereto, the transition metal is selected from the group consisting of Cu(II), Cu(III), Ni(II), Ni(III), Zn(II), Fe(II), Fe(III), Co(II), Co(III), Cr(II), and Cr(III).

11. The composition according to claim 1, wherein the first moiety comprises a naturally occurring polypeptide sequence which exhibits antimicrobial activity against an organism selected from the group consisting of a bacterium, a virus, a fungus, and a protozoan.

12. The composition according to claim 1, wherein the first moiety comprises a polypeptide sequence selected from the group consisting of Buforin, Pyrrhocoricin, ovispirin peptide OV-3, SMAP29, Histatin-5, Histatin-8, Histatin-2, CP10A, Bac2A, TriTrp1, Aurein 1.1, Magainin 1, Magainin 2, Indolicidin, and Bactenecin, and a mutein thereof.

13. The composition according to claim 1, wherein the first moiety comprises an antibiotic which exhibits antimicrobial activity against an organism selected from the group consisting of a bacterium, a virus, fungus, and a protozoan.

14. The composition according to claim 1, wherein the first moiety comprises an antibiotic selected from the group consisting of aminoglycosides, penicillins, cephalosporins, macrolides, sulfonamides, quinolones, and tetracyclines.

15. The composition according to claim 1, wherein the metal binding moiety comprises a peptide motif.

16. The composition according to claim 15, wherein said peptide motif coordinates a metal using amine, deprotonated backbone amide, or imidazole functionalities on the peptide motif.

17. The composition according to claim 1, wherein the composition comprises one or more poly(alkylene oxide) moieties covalently coupled thereto.

18. The composition according to claim 17, wherein the one or more poly(alkylene oxide) moieties are poly(ethylene glycol) (PEG) moieties having an average length between 4 and 1000 ethylene glycol monomeric units.

19. A method for antimicrobial therapy in a subject in need thereof, comprising: administering to the subject a composition according to claim 1 under conditions wherein the composition generates reactive oxygen species within a pathogenic microorganism or within a cell of the subject which contains a pathogenic microorganism, wherein the concentration of reactive oxygen species generated creates oxidative stress within the pathogenic microorganism or cell of the subject to antimicrobial effect.

20. A method for antimicrobial therapy in a subject in need thereof, comprising: administering to the subject a composition according to claim 1 under conditions wherein the composition functions as a Lewis acid and generates reactive hydrolytic species within a pathogenic microorganism, wherein the concentration of hydrolytic species generated creates subsequent chemical stress within the pathogenic microorganism or cell of the subject to antimicrobial effect.

21. A method for antimicrobial therapy in a subject in need thereof, comprising: administering to the subject a composition according to claim 17 under conditions wherein the composition generates reactive oxygen species within a pathogenic microorganism or within a cell of the subject which contains a pathogenic microorganism, wherein the concentration of reactive oxygen species generated creates oxidative stress within the pathogenic microorganism or cell of the subject to antimicrobial effect.

22. A method for antimicrobial therapy in a subject in need thereof, comprising: administering to the subject a composition according to claim 17 under conditions wherein the composition functions as a Lewis acid and generates reactive hydrolytic species within a pathogenic microorganism, wherein the concentration of hydrolytic species generated creates subsequent chemical stress within the pathogenic microorganism or cell of the subject to antimicrobial effect.

* * * * *